United States Patent
Lei

(10) Patent No.: US 7,312,063 B2
(45) Date of Patent: Dec. 25, 2007

(54) OVEREXPRESSION OF PHYTASE GENES IN YEAST SYSTEMS

(75) Inventor: Xingen Lei, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/372,851

(22) Filed: Mar. 10, 2006

(65) Prior Publication Data

US 2006/0153902 A1    Jul. 13, 2006

Related U.S. Application Data

(63) Continuation of application No. 10/094,693, filed on Mar. 8, 2002, now Pat. No. 7,026,150, which is a continuation-in-part of application No. 09/104,769, filed on Jun. 25, 1998, now Pat. No. 6,451,572.

(51) Int. Cl.
  C12N 9/16 (2006.01)
  C12N 1/20 (2006.01)
  C12N 1/14 (2006.01)
  C12N 15/00 (2006.01)
  C07H 21/04 (2006.01)

(52) U.S. Cl. ................ 435/196; 435/252.3; 435/320.1; 435/254.2; 435/254.21; 435/254.1; 435/254.23; 435/254.3; 536/23.2; 536/23.4; 536/23.7

(58) Field of Classification Search ................ 435/196, 435/252.3, 320.1, 254.1, 254.2, 254.21, 254.23, 435/254.3; 536/23.2, 23.4, 23.7
See application file for complete search history.

(56) References Cited

U.S. PATENT DOCUMENTS

| | | |
|---|---|---|
| 3,819,528 A | 6/1974 | Berry |
| 3,860,484 A | 1/1975 | O'Malley |
| 3,966,971 A | 6/1976 | Morehouse et al. |
| 4,038,140 A | 7/1977 | Jaworek et al. |
| 4,375,514 A | 3/1983 | Siewert et al. |
| 4,460,683 A | 7/1984 | Gloger et al. |
| 4,470,968 A | 9/1984 | Mitra et al. |
| 4,734,283 A | 3/1988 | Siren |
| 4,765,994 A | 8/1988 | Holmgren |
| 4,778,761 A | 10/1988 | Miyanohara et al. |
| 4,914,029 A | 4/1990 | Caransa et al. |
| 4,915,960 A | 4/1990 | Holmgren |
| 4,950,609 A | 8/1990 | Tischer et al. |
| 4,997,767 A | 3/1991 | Nozaki et al. |
| 5,024,941 A | 6/1991 | Maine et al. |
| 5,200,399 A | 4/1993 | Wettlaufer et al. |
| 5,268,273 A | 12/1993 | Buckholz |
| 5,290,765 A | 3/1994 | Wettlaufer et al. |
| 5,316,770 A | 5/1994 | Edwards, Jr. |
| 5,318,903 A | 6/1994 | Bewert et al. |
| 5,366,736 A | 11/1994 | Edwards, Jr. |
| 5,436,156 A | 7/1995 | Van Gorcom et al. |
| 5,443,979 A | 8/1995 | Vanderbeke et al. |
| 5,480,790 A | 1/1996 | Tischer et al. |
| 5,492,821 A | 2/1996 | Callstrom et al. |
| 5,516,525 A | 5/1996 | Edwards, Jr. |
| 5,554,399 A | 9/1996 | Vanderbeke et al. |
| 5,556,771 A | 9/1996 | Shen et al. |
| 5,593,963 A | 1/1997 | Van Ooijen et al. |
| 5,612,055 A | 3/1997 | Bedford et al. |
| 5,691,154 A | 11/1997 | Callstrom et al. |
| 5,716,655 A | 2/1998 | Hamstra et al. |
| 5,736,625 A | 4/1998 | Callstrom et al. |
| 5,780,292 A | 7/1998 | Nevalainen et al. |
| 5,827,709 A | 10/1998 | Barendse et al. |
| 5,830,696 A | 11/1998 | Short |
| 5,830,733 A | 11/1998 | Nevalainen et al. |
| 5,834,286 A | 11/1998 | Nevalainen et al. |
| 5,853,779 A | 12/1998 | Takebe et al. |
| 5,863,533 A | 1/1999 | Van Gorcom et al. |
| 5,876,997 A | 3/1999 | Kretz |
| 5,891,708 A | 4/1999 | Saniez et al. |
| 5,900,525 A | 5/1999 | Austin-Phillips et al. |
| 5,902,615 A | 5/1999 | Saniez et al. |
| 5,935,624 A | 8/1999 | DeLuca et al. |
| 5,955,448 A | 9/1999 | Colaco et al. |
| 5,972,669 A | 10/1999 | Harz et al. |
| 5,985,605 A | 11/1999 | Cheng et al. |

(Continued)

FOREIGN PATENT DOCUMENTS

| | | |
|---|---|---|
| CN | 1126243 A | 7/1996 |
| EP | 0 420 358 A1 | 4/1991 |
| EP | 0 449 376 A2 | 10/1991 |

(Continued)

OTHER PUBLICATIONS

Atlung et al., "Role of the Transcriptional Activator AppY in Regulation of the *cyx appA* Operon of *Escherichia coli* by Anaerobiosis, Phosphate Starvation, and Growth Phase," *Journal of Bacteriology* 176(17):5414-5422 (1994).

Belin et al., "A Pleiotropic Acid Phosphatase-Deficient Mutant of *Escherichia coli* Shows Premature Termination in the *dsbA* Gene. Use of *dsbA::phoA* Fusions to Localize a Structurally Important Domain in DsbA," *Mol. Gen. Genet.* 242:23-32 (1994).

Blondeau et al., "Development of High-Cell-Density Fermentation for Heterologous Interleukin 1β Production in *Kluyveromyces lactis* Controlled by the PHO5 Promoter," *Appl Microbiol Biotechnol*, 41:324-329 (1994).

(Continued)

*Primary Examiner*—Tekchand Saidha
(74) *Attorney, Agent, or Firm*—Nixon Peabody LLP

(57) ABSTRACT

The present invention relates to a method of producing a heterologous protein or polypeptide having phytase activity in a yeast system. The invention also provides proteins having phytase activity which have increased thermostability. Yeast strains which produce a heterologous phytase and the vectors used to produce the phytase are also provided.

27 Claims, 23 Drawing Sheets

U.S. PATENT DOCUMENTS

| | | | |
|---|---|---|---|
| 5,989,600 A | 11/1999 | Nielsen et al. | |
| 6,022,555 A | 2/2000 | DeLuca et al. | |
| 6,039,942 A | 3/2000 | Lassen et al. | |
| 6,063,431 A | 5/2000 | Bae et al. | |
| 6,083,541 A | 7/2000 | Hamstra et al. | |
| 6,110,719 A | 8/2000 | Kretz | |
| 6,139,892 A | 10/2000 | Fredlund et al. | |
| 6,139,902 A | 10/2000 | Kondo et al. | |
| 6,140,077 A | 10/2000 | Nakamura et al. | |
| 6,183,740 B1 | 2/2001 | Short et al. | |
| 6,190,897 B1 | 2/2001 | Kretz | |
| 6,204,012 B1 | 3/2001 | Hellmuth et al. | |
| 6,248,938 B1 | 6/2001 | Austin-Phillips et al. | |
| 6,261,592 B1 | 7/2001 | Nagashima et al. | |
| 6,264,946 B1 | 7/2001 | Mullertz et al. | |
| 6,274,178 B1 | 8/2001 | Beven et al. | |
| 6,277,623 B1 | 8/2001 | Oh et al. | |
| 6,284,502 B1 | 9/2001 | Maenz et al. | |
| 6,291,221 B1 | 9/2001 | van Loon et al. | |
| 6,309,870 B1 | 10/2001 | Kondo et al. | |
| 6,350,602 B1 | 2/2002 | Van Gorcom et al. | |
| 6,391,605 B1 | 5/2002 | Kostrewa et al. | |
| 6,451,572 B1 * | 9/2002 | Lei | 435/196 |
| 6,475,762 B1 | 11/2002 | Stafford et al. | |
| 6,511,699 B1 | 1/2003 | Lei | |
| 6,514,495 B1 | 2/2003 | Svendsen et al. | |
| 6,599,735 B1 | 7/2003 | Bartok et al. | |
| 6,720,174 B1 | 4/2004 | Lehmann | |
| 6,841,370 B1 | 1/2005 | Lei | |
| 6,974,690 B2 | 12/2005 | Lei | |
| 7,022,371 B2 | 4/2006 | Stafford et al. | |
| 7,026,150 B2 * | 4/2006 | Lei | 435/196 |
| 2001/0018197 A1 | 8/2001 | Wong et al. | |
| 2001/0029042 A1 | 10/2001 | Fouache et al. | |
| 2002/0068350 A1 | 6/2002 | Kondo et al. | |
| 2002/0102692 A1 | 8/2002 | Lei | |
| 2002/0127218 A1 | 9/2002 | Svendsen et al. | |
| 2002/0136754 A1 | 9/2002 | Short et al. | |
| 2003/0092155 A1 | 5/2003 | Kostrewa et al. | |
| 2003/0206913 A1 | 11/2003 | Webel et al. | |
| 2004/0126844 A1 | 7/2004 | Lei et al. | |
| 2005/0095691 A1 | 5/2005 | Lei | |

FOREIGN PATENT DOCUMENTS

| | | |
|---|---|---|
| EP | 0 556 883 A1 | 8/1993 |
| EP | 0 649 600 A1 | 4/1995 |
| EP | 0 684 313 A2 | 11/1995 |
| EP | 0 699 762 A2 | 3/1996 |
| EP | 0 772 978 B1 | 5/1997 |
| EP | 0 779 037 A1 | 6/1997 |
| EP | 0 897 010 A2 | 2/1999 |
| EP | 0 897 985 A2 | 2/1999 |
| EP | 0 909 821 A2 | 4/1999 |
| EP | 0 925 723 A1 | 6/1999 |
| EP | 0 955 362 A1 | 11/1999 |
| EP | 0 960 934 A1 | 12/1999 |
| GB | 2 286 396 A | 8/1995 |
| GB | 2 316 082 A | 2/1998 |
| JP | 10-276789 | 10/1998 |
| JP | 2001-292789 | 10/2001 |
| RU | 2 113 468 C1 | 6/1998 |
| WO | WO 86/01179 A1 | 2/1986 |
| WO | WO 90/03431 A1 | 4/1990 |
| WO | WO90/05182 | 5/1990 |
| WO | WO91/05053 | 4/1991 |
| WO | WO91/14773 | 10/1991 |
| WO | WO91/14782 | 10/1991 |
| WO | WO93/14645 | 8/1993 |
| WO | WO93/16175 | 8/1993 |
| WO | WO93/19759 | 10/1993 |
| WO | WO94/03072 | 2/1994 |
| WO | WO94/03612 | 2/1994 |
| WO | WO97/16076 | 5/1997 |
| WO | WO97/35017 | 9/1997 |
| WO | WO97/39638 | 10/1997 |
| WO | WO97/45009 | 12/1997 |
| WO | WO97/48812 | 12/1997 |
| WO | WO98/05785 | 2/1998 |
| WO | WO98/06856 | 2/1998 |
| WO | WO98/20139 | 5/1998 |
| WO | WO98/30681 | 7/1998 |
| WO | WO98/44125 | 10/1998 |
| WO | WO98/54980 | 12/1998 |
| WO | WO99/08539 | 2/1999 |
| WO | WO 99/49022 A1 | 9/1999 |
| WO | WO99/49740 | 10/1999 |
| WO | WO 00/10404 | 3/2000 |
| WO | WO 00/20569 | 4/2000 |
| WO | WO 00/41509 A3 | 7/2000 |
| WO | WO 00/43503 A1 | 7/2000 |
| WO | WO 00/47060 | 8/2000 |
| WO | WO 00/58481 A2 | 10/2000 |
| WO | WO 00/71728 A1 | 11/2000 |
| WO | WO 00/72700 A1 | 12/2000 |
| WO | WO 01/36607 A1 | 5/2001 |
| WO | WO 01/58275 A2 | 8/2001 |
| WO | WO 01/58276 A2 | 8/2001 |

OTHER PUBLICATIONS

Boctor et al., "Enhancement of the Stability of Thrombin by Polyols: Microcalorimetric Studies," *J. Pharm. Pharmacol.*, 44:600-603 (1992).

Boer et al., "Characterization of *Trichoderma reesei* Cellobiohydrolase Cel7a Secreted from *Pichia pastoris* Using Two Different Promoters," *Biotechnology and Bioengineering* 69(5):486-494 (2000).

Brondsted et al., "Effect of Growth Conditions on Expression of the Acid Phosphatase (*cyx-appA*) Operon and the *appY* Gene, Which Encodes a Transcriptional Activator of *Escherichia coli*," *J. of Bacteriology*, 178(6):1556-1564 (1996).

Chiarugi et al., "Differential Role of Four Cysteines on the Activity of a Low $M_r$ Phosphotyrosine Protein Phosphatase," *FEBS Letters* 310(1):9-12 (1992).

Dassa et al., "Identification of the Gene *appA* for the Acid Phosphatase (pH Optimum 2.5) of *Escherichia coli*," *Mol. Gen. Genet.*, 200:68-73 (1985).

Dassa et al., "The Complete Nucleotide Sequence of the *Escherichia coli* Gene *appA* Reveals Significant Homology Between pH 2.5 Acid Phosphatase and Glucose-1-Phosphatase," *J. of Bacteriology*, 172(9):5497-5500 (1990).

Divakaran et al., "*In vitro* Studies on the Interaction of Phytase with Trypsin and Amylase Extracted from Shrimp (*Penaeus vannamei*) Hepatopancreas," *J. Agric. Food Chem.* 46:4973-4976 (1998).

Greiner et al., "Purification and Characterization of Two Phytases from *Escherichia coli*," *Archives of Biochemistry and Biophysics*, 303:107-113 (1993).

Granovskii et al., "Expression of Hepatitis B Virus HBsAg Gene in Yeast Cells Under Control of Promotor Region of PHO5 Gene," *Soviet Progress in Virology*, 5:45-47 (1985).

Han et al., "Development of Phytase Overexpressing Microbes for Nutritional Use," Poster Presentation at Cornell University's Biotechnology Symposium, Ithaca, New York (Oct. 15, 1997).

Han et al., "Expression of an *Aspergillus niger* Phytase Gene (*phyA*) in *Saccharomyces cerevisiae*," *Applied and Environ. Microbiol.*, 65(5):1915-1918 (1999).

Han et al., "Role of Glycosylation in the Functional Expression of an *Aspergillus niger* Phytase (*phyA*) in *Pichia pastoris*," *Archives of Biochemistry and Biophysics*, 364:83-90 (1999).

Jia et al., "Purification, Crystallization and Preliminary X-ray Analysis of the *Escherichia coli* Phytase," *Acta Cryst.* D54:647-649 (1998).

Kanai et al., "Recombinant Thermostable Cycloinulo-oligosaccharide Fructanotransferase Produced by *Saccharomyces cerevisiae*," *Appl. Environ. Microbiol.* 63(12):4956-4960 (1997).

Kerovuo et al., "Isolation, Characterization, Molecular Gene Cloning, and Sequencing of a Novel Phytase from *Bacillus subtilis*," *Applied and Environmental Microbiology* 64(6):2079-2085 (1998).

Kim et al., "Cloning of the Thermostable Phytase Gene (*phy*) from *Bacillus* sp. DS11 and its Overexpression in *Escherichia coli*," *FEMS Microbiology Letters* 162:185-191 (1998).

Konietzny et al., "Model Systems for Developing Detection Methods for Foods Deriving from Genetic Engineering," *J. Food Composition and Analysis*, 10:28-35 (1997).

Kumagai et al., "Conversion of Starch to Ethanol in a Recombinant *Saccharomyces cerevisiae* Strain Expressing rice α-amylase from a Novel *Pichia pastoris* Alcohol Oxidase Promoter," *Biotechnology* 11:606-610 (1993).

Lei et al., "Nutritional Benefits of Phytase and Dietary Determinants of Its Efficacy," *J. Appl. Anim. Res.* 17:97-112 (2000).

Lei et al., "Biotechnological Developments of Effective Phytases for Mineral Nutrition and Environmental Protection," *Appl. Microb. Biotech.* 57(4):474-481 (2001).

Lim et al., "Crystal Structure of *Escherichia coli* Phytase and its Complex with Phytate," *Nature Structural Biology* 7(2): 108-113 (2000).

Lim et al., "Studies of Reaction Kinetics in Relation to the $T_g'$ of Polymers in Frozen Model Systems," in Levine, eds., *Water Relationships in Food*, New York, NY:Plenum Press, pp. 103-122 (1991).

Lozano et al., "Influence of Polyhydroxylic Cosolvents on Papain Thermostability," *Enzyme Microb. Technol.*, 15:868-873 (1993).

Lozano et al., "Effect of Polyols on α-Chymotrypsin Thermostability: A Mechanistic Analysis of the Enzyme Stabilization," *J. Biotechnol.*, 35:9-18 (1994).

Maugenest et al., "Cloning and Characterization of cDNA Encoding a Maize Seedling Phytase," *Biochem. J.* 322:511-517 (1997).

Meldgaard et al., "Different Effects of N-Glycosylation on the Thermostability of Highly Homologous Bacterial (1,3-1,4)-β-Glucanases Secreted from Yeast," *Microbiology* 140(1):159-166 (1994).

Minamiguchi et al., "Secretive Expression of the *Aspergillus aculeatus* Cellulase (FI-CM Case) by *Saccharomyces cerevisiae*," *J. Fermentation and Bioengineering*, 79(4):363-366 (1995).

Moore et al., "Molecular Cloning, Expression and Evaluation of Phosphohydrolases for Phytate-Degrading Activity," *Journal of Industrial Microbiology*, 14:396-402 (1995).

Murray et al., "Construction of Artificial Chromosomes in Yeast," *Nature* 305:189-193 (1983).

Ostanin et al., "Overexpression, Site-Directed Mutagenesis, and Mechanism of *Escherichia coli* Acid Phosphatase," *J. of Biol. Chem.*, 267(32):22830-22836 (1992).

Ostanin et al., "Asp$^{304}$ of *Escherichia coli* Acid Phosphatase is Involved in Leaving Group Protonation," *J. of Biol. Chem.*, 268(28):20778-20784 (1993).

Phillippy et al., "Expression of an *Aspergillus niger* Phytase (*phyA*) in *Escherichia coli*," *J. Agric. Food Chem.* 45(8):3337-3342 (1997).

Piddington et al., "The Cloning and Sequencing of the Genes Encoding Phytase (*phy*) and pH 2.5-Optimum Acid Phosphatase (*aph*) From *Aspergillus niger* var. *awamori*," *Gene*, 133:55-62 (1993).

Rodriguez et al., "Different Sensitivity of Recombinant *Aspergillus niger* Phytase (r-PhyA) and *Escherichia coli* pH 2.5 Acid Phosphatase (r-AppA) to Trypsin and Pepsin *In vitro*," *Archives of Biochemistry and Biophysics* 365(2):262-267 (1999).

Rodriguez et al., "Cloning, Sequencing, and Expression of an *Escherichia coli* Acid Phosphatase/Phytase Gene (*appA2*) Isolated from Pig Colon," *Biochemical and Biophysical Research Communications*, 257:117-123 (1999).

Rodriguez et al., "Site-Directed Mutagenesis Improves Catalytic Efficiency and Thermostability of *Escherichia coli* pH 2.5 Acid Phosphatase/Phytase Expressed in *Pichia pastoris*," *Archives of Biochemistry and Biophysics* 382(1):105-112 (2000).

Rossi et al., "Stabilization of the Restriction Enzyme EcoRI Dried with Trehalose and Other Selected Glass-Forming Solutes," *Biotechnol. Prog.*, 13:609-616 (1997).

Schebor et al., "Glassy State and Thermal Inactivation of Invertase and Lactase in Dried Amorphous Matrices," *Biotechnol. Prog.*, 13:857-863 (1997).

Sidhu et al., "Analysis of α-Factor Secretion Signals by Fusing with Acid Phosphatase of Yeast," *Gene*, 54:175-184 (1987).

Sun et al., "Expression of *Aspergillus niger* Phytase in Yeast *Saccharomyces cerevisiae* for Poultry Diet Supplementation," *Poultry Science* 76(Suppl. 1):5 (1997).

Takahashi et al., "Independent Production of Two Molecular Forms of a Recombinant *Rhizopus oryzae* Lipase by *KEX2*-Engineered Strains of *Saccharomyces cerevisiae*," *Applied Microbiol. Biotechnology*, 52(4):534-540 (1999).

Terashima et al., "The Roles of the N-Linked Carbohydrate Chain of Rice α-amylase in Thermostability and Enzyme Kinetics," *Eur. J. Biochem.* 226:249-254 (1994).

Touati et al., "Pleiotropic Mutations in *appR* Reduce pH 2.5 Acid Phosphatase Expression and Restore Succinate Utilisation in CRP-Deficient Strains of *Escherichia coli*," *Mol. Gen. Genet.* 202:257-264 (1986).

Tschopp et al., "Heterologous Gene Expression in Methylotrophic Yeast," *Biotechnology*, 18:305-322 (1991).

Van Hartingsveldt et al., "Cloning, Characterization and Overexpression of the Phytase-Encoding Gene (*phyA*) of *Aspergillus niger*," *Gene* 127:87-94 (1993).

Verwoerd et al., "Stable Accumulation of *Aspergillus niger* Phytase in Transgenic Tobacco Leaves," *Plant Physiol.*, 109:1199-1205(1995).

Wodzinski et al., "Phytase," *Advances in Applied Microbiology*, 42:263-302 (1996).

Wyss et al., "Biochemical Characterization of Fungal Phytases (*myo*-Inositol Hexakisphosphate Phosphohydrolases): Catalytic Properties," *Applied and Environmental Microbiology* 65(2):367-373 (1999).

Wyss et al., "Biophysical Characterizartion of Fungal Phytases (*myo*-Inositol Hexakisphosphate Phosphohydrolases): Molecular Size, Glycosylation Pattern, and Engineering of Proteolytic Resistance," *Applied and Environ. Microbiol.*, 65(2):359-366 (1999).

Yao et al., "Recombinant *Pichia pastoris* Overexpressing Bioactive Phytase," *Science in China Series C. Life Sciences*, 41(3):330-336 (1998).

Zvonok et al., "Construction of Versatile *Escherichia coli*-Yeast Shuttle Vectors for Promoter Testing in *Saccharomyces cerevisiae*," *Gene*, 66(2):313-318 (1988).

Greiner et al., "Purification and Characterization of a Phytase from *Klebsiella terrigena*," Archives of Biochemistry and Biophysics 341(2):201-206 (1997).

Ullah, A.H.J., "*Aspergillus Ficuum* Phytase: Partial Primary Structure, Substrate Selectivity, and Kinetic Characterization," Preparative Biochemistry 18(4):459-471 (1988).

DSM NUTRITIONAL PRODUCTS, Opposition Brief for European Patent No. EP 1-090-129 (10 pages) (Nov. 15, 2006).

NOVOZYMES A/S, Opposition Brief for European Patent No. EP 1-090-129 (19 pages) (Nov. 2006).

ATCC Catalog for Yeasts, 19th Edition (1995).

DATABASE ACCESSION No. B36733, corresponding to Greiner et al., Arch. Biochem. Biophys. 303:107-113 (1993).

GENBANK ACCESSION No. AAB96872 (Jan. 16, 1998).

GENBANK ACCESSION No. M94550 (Apr. 27, 1993).

GENBANK ACCESSION No. P34752 (Jan. 25, 2005).

Golovan et al., "Characterization and Overproduction of the E. coli appA Encoded Biofunctional Enzyme the Exhibits Both Phytase and Acid Phosphatase Activities," *Can. J. Microbiol.* 46:59-71 (2000).

Kostrewa et al., "Crystal Structure of *Aspergillus niger* pH 2.5 Acid Phosphatase at 2.4 Å Resolution," *Mol. Biol.* 288:965-974 (1999).

Kostrewa et al., "Crystal Structure of Phytase from *Aspergillus ficuum* at 2.5 Å Resolution," *Nat. Struct. Biol.* 4:185-190 (1997).

Leeson et al., "Efficacy of New Bacterial Phytase in Poultry Diets," *Can. J. Anim. Sci.* 80:527-528 (2000).

Lehmann et al., "Exchanging the Active Site Between Phytases for Altering the Functional Properties of the Enzyme," *Protein Sci.* 9(10):1866-1872 (2000).

Lehmann et al., "From DNA Sequence to Improved Functionality: Using Protein Sequence Comparisons to Rapidly Design a Thermostable Consensus Phytase," *Protein Eng.* 13(1):49-57 (2000).

Lei et al., "Calcium Level Affects the Efficacy of Supplemental Microbial Phytase in Corn-Soybean Meal Diets of Weanling Pigs," *J. Anim. Sci.* 72(1):139-143 (1994).

Lei et al., "Supplemental Microbial Phytase Improves Bioavailability of Dietary Zinc to Weanling Pigs," *J. Nutr.* 123:1117-1123 (1993).

Lei et al., "Supplementing Corn-Soybean Meal Diets with Microbial Phytase Linearly Improves Phytate Phosphorus Utilization by Weanling Pigs," *J. Anim. Sci.* 71:3359-3367 (1993).

Mitchell et al., "The Phytase Subfamily of Histidine Acid Phosphatases: Isolation of Genes for Two Novel Phytase from the Fungi *Aspergillus terreus* and *Myceliophthora thermophila,*" *Microbiol.* 143:245-252 (1997).

Mullaney et al., "Advances in Phytase Research," *Adv. Appl. Microbiol.* 47:157-199 (2000).

Mullaney et al., "Phytase Activity in *Aspergillus fumigatus* Isolates," *Biochem. Biophys. Res. Commun.* 275:759-763 (2000).

Mullaney et al., "Positive Identification of a Lambda gt11 Clone Containing a Region of Fungal Phytase Gene by Immunoprobe and Sequence Verification," *Appl. Microbiol. Biotechnol.* 35:611-614 (1991).

Mullaney et al., "Site-Directed Mutagenesis of *Aspergillus niger* NRRL 3135 Phytase at Residue 300 to Enhance Catalysis at pH 4.0," *Biochem. Biophys. Res. Commun.* 297(4):1016-1020 (2002).

Murry et al., "The Effect of Microbial Phytase in a Pearl Millet-Soybean Meal Diet on Apparent Digestibility and Retention of Nutrients, Serum Mineral Concentration, and Bone Mineral Density of Nursery Pigs," *J. Animal Sci.* 75:1284-1291 (1997).

Nielsen et al., "The Determinants of α-Amylase pH-Activity Profiles," *Protein Eng.* 14(7):505-512 (2001).

Pasamontes et al., "Gene Cloning, Purification, and Characterization of a Heat-Stable Phytase from the Fungus *Aspergillus fumigatus,*" *Appl. Environ. Microbiol.* 63(5):1696-1700 (1997).

Rodriguez et al., "Expression of the *Aspergillus fumigatus* Phytase Gene in *Pichia pastoris* and Characterization of the Recombinant Enzyme," *Biochem. Biophys. Res. Commun.* 268:373-378 (2000).

Scott et al., "The Effect of Phosphorus, Phytase Enzyme, and Calcium on the Performance of Layers Fed Corn-Based Diets," *Poultry Sci.* 78:1742-1749 (1999).

Sebastian et al., "Apparent Digestibility of Protein and Amino Acids in Brioler Chickens Fed a Corn-Soybean Diet Supplemented with Microbial Phytase," *Poultry Sci.* 76:1760-1769 (1997).

Tomschy et al., "Active Site Residue 297 of *Aspergillus niger* Phytase Critically Affects the Catalytic Properties," *FEBS Lett.* 472(2-3):169-172 (2000).

Tomschy et al., "Engineering of Phytase for Improved Activity at Low pH," *Appl. Environ. Microbiol.* 68(4):1907-1913 (2002).

Tomschy et al., "Optimization of the Catalytic Properties of *Aspergillus fumigatus* Phytase Based on the Three-Dimensional Structure," *Protein Sci.* 9(7):1304-1311 (2000).

Ullah et al., "Cyclohexanedione Modification of Arginine at the Active Site of *Aspergillus ficuum* Phytase," *Biochem. Biophys. Res. Commun.* 178(1):45-53 (1991).

Ullah et al., "Extracellular Phytase (E.C. 3.1.3.8) from *Aspergillus ficuum* NRRL 3135: Purification and Characterization," *Prep. Biochem.* 17(1):63-91 (1987).

Van Dijck, P.W.M., "Chymosin and Phytase. Made by Genetic Engineering (No. 10 in a Series of Articles to Promote a Better Understanding of the Use of Genetic Engineering)," *J. Biotechnol.* 67:77-80 (1999).

Van Etten et al., "Covalent Structure, Disulfide Bonding, and Identification of Reactive Surface and Active Site Residues of Human Prostatic Acid Phosphatase," *J. Biol. Chem.* 266(4):2313-2319 (1991).

Yi et al., "Sites of Phytase Activity in the Gastrointestinal Tract of Young Pigs," *Anim. Feed Sci. Technol.* 61:361-368 (1996).

Ullah et al., "Differences in the Active Site Environment of *Aspergillus ficuum* Phytases," *Biochem. Biophys. Res. Comm.* 243:458-462 (1998).

* cited by examiner

OVEREXPRESSION OF PHYTASE GENES IN YEAST SYSTEMS

This application is a continuation of U.S. patent application Ser. No. 10/094,693, filed Mar. 8, 2002, now U.S. Pat. No. 7,026,150, issued Apr. 11, 2006, which is a continuation-in-part of U.S. patent application Ser. No. 09/104,769, filed Jun. 25, 1998, now U.S. Pat. No. 6,451,572, issued Sep. 17, 2002, which are hereby incorporated by reference in their entirety.

FIELD OF THE INVENTION

The present invention relates to a method of producing phytase in yeast, yeast strains which express heterologous phytase, and the heterologous phytase produced by yeast.

BACKGROUND OF THE INVENTION

Phytases, a specific group of monoester phosphatases, are required to initiate the release of phosphate ("P") from phytate (myo-inositol hexophosphate), the major storage form of P in cereal foods or feeds (Reddy, N. R. et al., "Phytates in Legumes and Cereals," *Advances in Food Research*, 28:1 (1982)). Because simple-stomached animals like swine and poultry as well as humans have little phytase activity in their gastrointestinal tracts, nearly all of the ingested phytate P is indigestible. This results in the need for supplementation of inorganic P, an expensive and non-renewable nutrient, in diets for these animals. More undesirably, the unutilized phytate-P excreted through manure of these animals becomes P pollution of the environment (Cromwell, G. L. et al., "P-A Key Essential Nutrient, Yet a Possible Major Pollutant—Its Central Role in Animal Nutrition," *Biotechnology In the Feed Industry*; Proceedings Alltech 7th Annual Symposium, p. 133 (1991)). Furthermore, phytate chelates with essential trace elements like zinc and produces nutrient deficiencies such as growth and mental retardation in children ingesting mainly plant origin foods without removal of phytate.

Two phytases, phyA and phyB, from *Aspergillus niger* NRRL3135 have been cloned and sequenced (Ehrlich, K. C. et al., "Identification and Cloning of a Second Phytase Gene (phys) from *Aspergillus niger (ficuum)*," *Biochem. Biophys. Res. Commun.*, 195:53–57 (1993); Piddington, C. S. et al., "The Cloning and Sequencing of the Genes Encoding Phytase (phy) and pH 2.5-optimum Acid Phosphatase (aph) from *Aspergillus niger* var. *awamori*," *Gene*, 133:56–62 (1993)). Recently, new phytase genes have been isolated from *Aspergillus terreus* and *Myceliophthora thermophila* (Mitchell et al., "The Phytase Subfamily of Histidine Acid Phosphatases: Isolation of Genes for Two Novel Phytases From the Fungi *Aspergillus terreus* and *Myceliophthora thermophila*," *Microbiology* 143:245–252, (1997)), *Aspergillus fumigatus* (Pasamontes et al., "Gene Cloning, Purification, and Characterization of a Heat-Stable Phytase from the Fungus *Aspergillus fumigatus*" *Appl. Environ. Microbiol.*, 63:1696–1700 (1997)), *Emericella nidulans* and *Talaromyces thermophilus* (Pasamontes et al., "Cloning of the Phytase from *Emericella nidulans* and the Thermophilic Fungus *Talaromyces thermophilus*," *Biochim. Biophys. Acta.*, 1353:217–223 (1997)), and maize (Maugenest et al., "Cloning and Characterization of a cDNA Encoding a Maize Seedling Phytase," *Biochem. J.* 322:511–517, 1997)).

Various types of phytase enzymes have been isolated and/or purified from *Enterobacter* sp. 4 (Yoon et al., "Isolation and Identification of Phytase-Producing Bacterium, *Enterobacter* sp. 4, and Enzymatic Properties of Phytase Enzyme," *Enzyme and Microbial Technology* 18:449–454 (1996)), *Klebsiella terrigena* (Greiner et al., "Purification and Characterization of a Phytase from *Klebsiella terrigena.*," *Arch. Biochem. Biophys.* 341:201–206 (1997)), and *Bacillus* sp. DS11 (Kim et al., "Purification and Properties of a Thermostable Phytase from *Bacillus* sp. DS11," *Enzyme and Microbial Technology* 22:2–7 (1998)). Properties of these enzyme have been studied. In addition, the crystal structure of phy A from *Aspergillus ficuum* has been reported (Kostrewa et al., "Crystal Structure of Phytase from *Aspergillus ficuum* at 2.5 A Resolution," *Nature Structure Biology* 4:185–190 (1997)).

Hartingsveldt et al. introduced phyA gene into *A. niger* and obtained a ten-fold increase of phytase activity compared to the wild type. ("Cloning, Characterization and Overexpression of the Phytase-Encoding Gene (phyA) of *Aspergillus Niger*," *Gene* 127:87–94 (1993)). Supplemental microbial phytase of this source in the diets for pigs and poultry has been shown to be effective in improving utilization of phytate-P and zinc (Simons et al., "Improvement of Phosphorus Availability By Microbial Phytase in Broilers and Pigs," *Br. J. Nutr.*, 64:525 (1990); Lei, X. G. et al., "Supplementing Corn-Soybean Meal Diets With Microbial Phytase Linearly Improves Phytate P Utilization by Weaning Pigs," *J. Anim. Sci.*, 71:3359 (1993); Lei, X. G. et al., "Supplementing Corn-Soybean Meal Diets With Microbial Phytase Maximizes Phytate P Utilization by Weaning Pigs," *J. Anim. Sci.*, 71:3368 (1993); Cromwell, G. L. et al., "P-A Key Essential Nutrient, Yet a Possible Major Pollutant—Its Central Role in Animal Nutrition," *Biotechnology In the Feed Industry*; Proceedings Alltech 7th Annual Symposium, p. 133 (1991)). But, expenses of the limited available commercial phytase supply and the activity instability of the enzyme to heat of feed pelleting preclude its practical use in animal industry (Jongbloed, A. W. et al., "Effect of Pelleting Mixed Feeds on Phytase Activity and Apparent Absorbability of Phosphorus and Calcium in Pigs," *Animal Feed Science and Technology*, 28:233–242 (1990)). Moreover, phytase produced from *A. niger* is presumably not the safest source for human food manufacturing.

Yeast can be used to produce enzymes effectively while grown on simple and inexpensive media. With a proper signal sequence, the enzyme can be secreted into the media for convenient collection. Some yeast expression systems have the added advantage of being well accepted in the food industry and are safe and effective producers of food products.

*Pichia pastoris* is a methylotrophic yeast, capable of metabolizing methanol as its sole carbon source. This system is well-known for its ability to express high levels of heterologous proteins. Because it is an eukaryote, *Pichia* has many of the advantages of higher eukaryotic expression systems such as protein processing, folding, and post-transcriptional modification.

Thus, there is a need to develop an efficient and simple system to produce phytase economically for the application of food and feed industry.

SUMMARY OF THE INVENTION

The present invention relates to a method of producing phytase in yeast by introducing a heterologous gene which encodes a protein or polypeptide with phytase/acid phosphatase activity into a yeast strain and expressing that gene.

The present invention also relates to a protein or polypeptide having phytase activity with optimum activity in a temperature range of 57–65° C. at pH of 2.5 to 3.5 or of 5.5. Optimal pH at 2.5 to 3.5 is particularly important for phytase, because that is the stomach pH of animals.

The invention further provides a yeast cell carrying a heterologous gene which encodes a protein or polypeptide with phytase activity and which is functionally linked to a promoter capable of expressing phytase in yeast.

Yet another aspect of the invention is a vector having a gene from a non-yeast organism which encodes a protein or polypeptide with phytase activity, a promoter which is capable of initiating transcription in yeast functionally linked to the gene encoding a peptide with phytase activity, and with an origin of replication capable of maintaining the vector in yeast or being capable of integrating into the host genome.

The invention also provides a method for producing a protein or polypeptide having phytase activity. An isolated appA gene, which encodes a protein or polypeptide with phytase activity, is expressed in a host cell.

The invention also includes a method of converting phytate to inositol and inorganic phosphate. The appA gene expresses a protein of polypeptide with phytase activity in a host cell. The protein or polypeptide is then contacted with phytate to catalyze the conversion of phytate to inositol and inorganic phosphate.

DETAILED DESCRIPTION OF THE INVENTION

Figure 1:
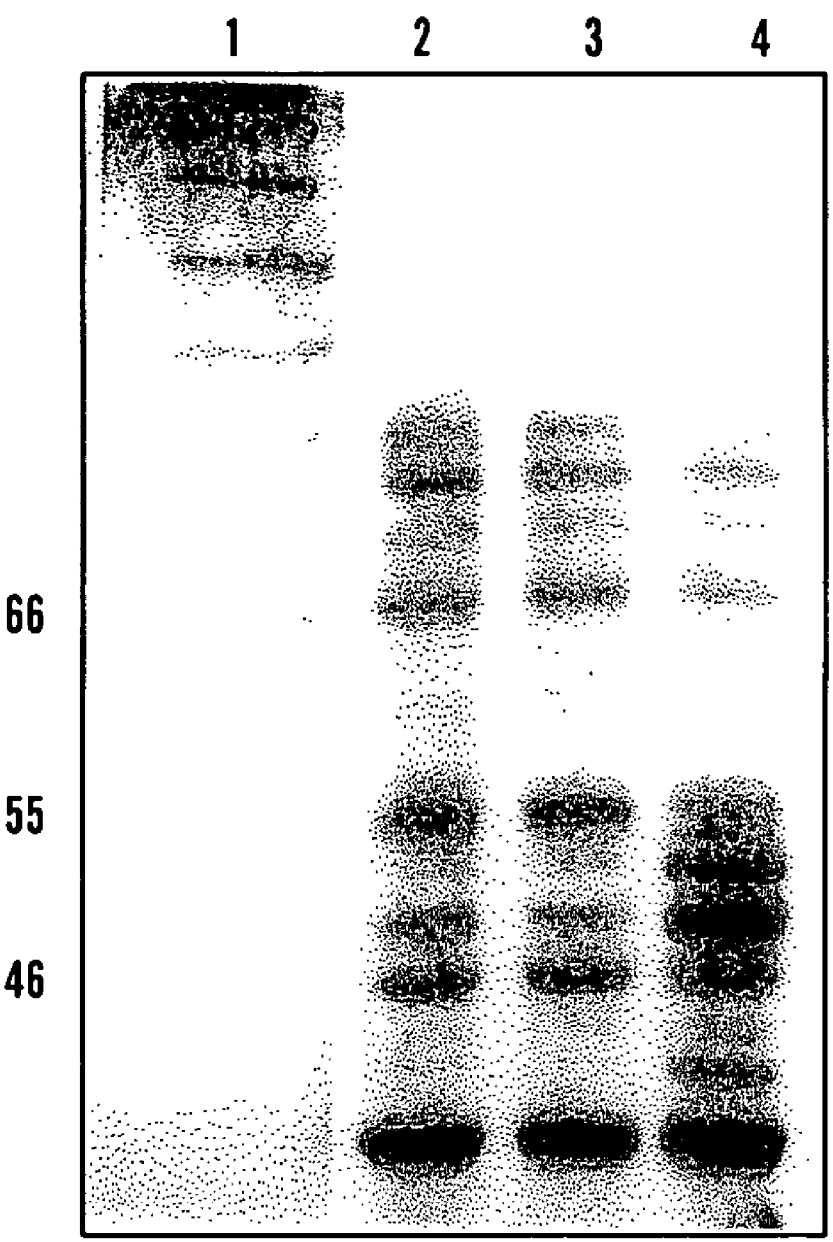
FIG. 1 shows an SDS-PAGE analysis of soluble protein prepared from the phytase gene transformed *E. coli* induced with IPTG. The cells were grown 4 hours before harvesting. Lane 1: Marker; Lanes 2 and 3: Transformants of pEP1 (the expressed protein was approximately 55 kDa); Lane 4: Transformant with only the expression vector pET25b(+).

The present invention provides a method of producing phytase in yeast. According to this method, a heterologous gene which encodes a protein or polypeptide with phytase activity is expressed in a yeast strain.

The enzymes which catalyze the conversion of phytate to inositol and inorganic phosphorus are broadly known as phytases. Phytase producing microorganisms comprise bacteria such as *Bacillus subtilis* (Paver et al., J. Bacteriol. 151, 1102 (1982), which is hereby incorporated by reference) and *Pseudomonas* (Cosgrove, Austral. J. Biol. Sci. 23:1207 (1970), which is hereby incorporated by reference); yeasts, such as *Saccharomyces cerevisiae* (Nayini et al., Lebensmittel Wissenschaft und Technologie 17:24 (1984), which is hereby incorporated by reference); and fungi, such as *Aspergillus terreus* (Yamada et al., Agric. Biol. Chem. 32:1275 (1986), which is hereby incorporated by reference), and *Aspergillus ficuum* (van Gorcom et al., European Patent Application 89/202,436, which is hereby incorporated by reference).

Phytases are also endogenously present in many plant species. Loewus, In: *Plant Biology* vol. 9: "Inositol Metabolism in Plants" (eds. D. J. Morre, W. F. Boss, F. A. Loewus) 13 (1990); and Gellatly, et al., Plant Physiology (supplement) 93:562 (1990), which are hereby incorporated by reference, mention the isolation and characterization of a phytase cDNA clone obtained from potato tubers. Gibson, et al., J. Cell Biochem., 12C:L407 (1988) and Christen, et al., J. Cell Biochem., 12C:L402 (1988), which are hereby incorporated by reference, mentions the synthesis of endogenous phytase during the germination of soybean seeds.

Preferably, the protein or polypeptide with phytase activity is secreted by the cell into growth media. This allows for higher expression levels and easier isolation of the product. The protein or polypeptide with phytase activity is coupled to a signal sequence capable of directing the protein out of the cell. Preferably, the signal sequence is cleaved from the protein.

In a preferred embodiment, the heterologous gene, which encodes a protein or polypeptide with phytase activity, is spliced in frame with a transcriptional enhancer element.

Preferred heterologous genes encoding proteins with phytase activity are isolated from a bacterial cell. A more preferred gene is the phyA gene of *Aspergillus niger*. A gene encoding phytase, phyA, from *Aspergillus niger* NRRL3135 has been cloned and sequenced (Piddington, C. S. et al., "The Cloning and Sequencing of the Genes Encoding Phytase (phy) and pH 2.5-optimum Acid Phosphatase (aph) from *Aspergillus niger* var. *awamori*," Gene, 133:56–62 (1993), which are hereby incorporated by reference). Hartingsveldt et al. introduced phyA gene into *A. niger*, and obtained a tenfold increase of phytase activity compared to the wild type. (Hartingsveldt et al., "Cloning, Characterization and Overexpression of the Phytase-Encoding Gene (phyA) of *Aspergillus Niger*," Gene 127:87–94 (1993), which is hereby incorporated by reference.)

Another preferred heterologous gene is the appA gene of *E. coli*. The gene, originally defined as *E. coli* periplasmic phosphoanhydride phosphohydrolase (appA) gene, contains 1,298 nucleotides (GeneBank accession number: M58708). The gene was first found to code for an acid phosphatase protein of optimal pH of 2.5 (EcAP) in *E. coli*. The acid phosphatase is a monomer with a molecular mass of 44,644 daltons. Mature EcAP contains 410 amino acids (Dassa, J. et al., "The Complete Nucleotide Sequence of the *Escherichia Coli* Gene AppA Reveals Significant Homology Between Ph 2.5 Acid Phosphatase and Glucose-1-Phosphatase," J. Bacteriology, 172:5497–5500 (1990), which is hereby incorporated by reference). Ostanin, et al. overexpressed appA in *E. coli* BL21 using a pT7 vector and increased its acid phosphatase activity by approximately 400-folds (440 mU/mg protein) (Ostanin, K. et al., "Overexpression, Site-Directed Mutagenesis, and Mechanism of *Escherichia Coli* Acid Phosphatase," J. Biol. Chem., 267:22830–36 (1992), which is hereby incorporated by reference). The product of the appA gene was not previously known to have phytase activity.

The appA or phyA gene can be expressed in any prokaryotic or eukaryotic expression system. A variety of host-vector systems may be utilized to express the protein-encoding sequence(s). Preferred vectors include a viral vector, plasmid, cosmid or an oligonucleotide. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Preferred hosts for expressing appA or phyA include fungal cells, including species of yeast or filamentous fungi, may be used as host cells in accordance with the present invention. Preferred yeast host cells include different strains of *Saccharomyces cerevisiae*. Other yeasts like *Kluyveromyces*, *Torulaspora*, and *Schizosaccharomyces* can also be used. In a preferred embodiment, the yeast strain used to overexpress the protein is *Saccharomyces cerevisiae*. Preferred filamentous fungi host cells include *Aspergillus* and *Neurospora*. A more preferred strain of *Aspergillus* is *Aspergillus niger*.

In another preferred embodiment of the present invention, the yeast strain is a methylotrophic yeast strain. Methylotrophic yeast are those yeast genera capable of utilizing methanol as a carbon source for the production of the energy resources necessary to maintain cellular function and containing a gene for the expression of alcohol oxidase. Typical methylotrophic yeasts include members of the genera *Pichia*, *Hansenula*, *Torulopsis*, *Candida*, and *Karwinskia*. These yeast genera can use methanol as a sole carbon source. In a more preferred embodiment, the methylotrophic yeast strain is *Pichia pastoris*.

The present invention also provides a protein or polypeptide with phytase activity. PhyA is expressed in *Pichia* and the resulting protein produced has much higher extracellular activity (~65 mU/ml). The phytase activity yield was approximately 30-fold greater than that in phyA transformed *Saccharomyces cerevisiae,* 21-fold greater than that in wild type of *Aspergillus niger,* and 65,000-fold greater than that in the untransformed *Pichia.* The optimal pH of the expressed phytase was 2.5 and 5.5, and the optimal temperature was 60° C. Similarly, appA is expressed in *Pichia* and *Saccharomyces cerevisiae* with the resulting protein having much higher extracellular activity and a much preferred optimal pH of 2.5 to 3.5.

A preferred embodiment of the invention is a protein or polypeptide having phytase activity with optimum activity in a temperature range of 57 to 65° C. A more preferred embodiment is a protein or polypeptide having phytase activity, where its temperature range for optimum activity is from 58 to 62° C.

Yet another preferred embodiment is a protein or polypeptide having phytase activity where the protein retains at least 40% of its activity after heating the protein for 15 minutes at 80° C. More preferred is a protein or polypeptide having phytase activity where the protein retains at least 60% of its activity after heating the protein for 15 minutes at 60° C.

Purified protein may be obtained by several methods. The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The present invention also provides a yeast strain having a heterologous gene which encodes a protein or polypeptide with phytase activity. The heterologous gene should be functionally linked to a promoter capable of expressing phytase in yeast.

Yet another aspect of the invention is a vector for expressing phytase in yeast. The vector carries a gene from a non-yeast organism which encodes a protein or polypeptide with phytase activity. The phytase gene can be cloned into any vector which replicates autonomously or integrates into the genome of yeast. The copy number of autonomously replicating plasmids, e.g. YEp plasmids may be high, but their mitotic stability may be insufficient (Bitter et al., "Expression and Secretion Vectors for Yeast," *Meth. Enzymol.* 153:516–44 (1987), which is hereby incorporated by reference). They may contain the 2 mu-plasmid sequence responsible for autonomous replication, and an *E. coli* sequence responsible for replication in *E. coli.* The vectors preferably contain a genetic marker for selection of yeast transformants, and an antibiotic resistance gene for selection in *E. coli.* The episomal vectors containing the ARS and CEN sequences occur as a single copy per cell, and they are more stable than the YEp vectors. Integrative vectors are used when a DNA fragment is integrated as one or multiple copies into the yeast genome. In this case, the recombinant DNA is stable and no selection is needed (Struhl et al., "High-Frequency Transformation of Yeast: Autonomous Replication of Hybrid DNA Molecules," *Proc. Nat'l Acad. Sci. USA* 76:1035–39 (1979); Powels et al., *Cloning Vectors, I-IV,* et seq. Elsevier, (1985); Sakai et al., "Enhanced Secretion of Human Nerve Growth Factor from *Saccharomyces Cerevisiae* Using an Advanced δ-Integration System," *Biotechnology* 9:1382–85 (1991), which are hereby incorporated by reference). Some vectors have an origin of replication, which functions in the selected host cell. Suitable origins of replication include 2μ, ARS1, and 25 μM. The vectors have restriction endonuclease sites for insertion of the fusion gene and promoter sequences, and selection markers. The vectors may be modified by removal or addition of restriction sites, or removal of other unwanted nucleotides.

The phytase gene can be placed under the control of any promoter (Stetler et al., "Secretion of Active, Full- and Half-Length Human Secretory Leukocyte Protease Inhibitor by *Saccharomyces cerevisiae,*" *Biotechnology* 7:55–60, (1989), which is hereby incorporated by reference). One can choose a constitutive or regulated yeast promoter. Suitable promoter sequences for yeast vectors include, among others, promoters for metallothionein, 3-phosphoglycerate kinase (Hitzeman et al., *J. Biol. Chem.* 255:2073 (1980), which is hereby incorporated by reference) or other glycolytic enzymes (Hess et al., *J. Adv. Enzyme Reg.* 7:149 (1968); and Holland et al., *Biochem.* 17:4900, (1978), which are hereby incorporated by reference), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in EP A-73,657 to Hitzeman, which is hereby incorporated by reference. Another alternative is the glucose-repressible ADH2 promoter described by Russell et al., *J. Biol. Chem.* 258:2674 (1982) and Beier et al., *Nature* 300:724 (1982), which are hereby incorporated by reference.

One can choose a constitutive or regulated yeast promoter. The strong promoters of e.g., phosphoglycerate kinase (PGK) gene, other genes encoding glycolytic enzymes, and the alpha -factor gene, are constitutive. When a constitutive promoter is used, the product is synthesized during cell growth. The ADH2 promoter is regulated with ethanol and glucose, the GAL-1-10 and GAL7 promoters with galactose and glucose, the PHO5 promoter with phosphate, and the metallothionine promoter with copper. The heat shock promoters, to which the HSP150 promoter belongs, are regulated by temperature. Hybrid promoters can also be used. A regulated promoter is used when continuous expression of the desired product is harmful for the host cells. Instead of yeast promoters, a strong prokaryotic promoter such as the T7 promoter, can be used, but in this case the yeast strain has to be transformed with a gene encoding the respective polymerase. For transcription termination, the HSP150 terminator, or any other functional terminator is used. Here, promoters and terminators are called control elements. The present invention is not restricted to any specific vector, promoter, or terminator.

The vector may also carry a selectable marker. Selectable markers are often antibiotic resistance genes or genes capable of complementing strains of yeast having well characterized metabolic deficiencies, such as tryptophan or histidine deficient mutants. Preferred selectable markers include URA3, LEU2, HIS3, TRP1, HIS4, ARG4, or antibiotic resistance genes.

The vector may also have an origin of replication capable of replication in a bacterial cell. Manipulation of vectors is more efficient in bacterial strains. Preferred bacterial origin of replications are ColE1, Ori, or oriT.

A leader sequence either from the yeast or from phytase genes or other sources can be used to support the secretion of expressed phytase enzyme into the medium. The present invention is not restricted to any specific type of leader sequence or signal peptide.

Suitable leader sequences include the yeast alpha factor leader sequence, which may be employed to direct secretion of the phytase. The alpha factor leader sequence is often inserted between the promoter sequence and the structural gene sequence (Kurjan et al., Cell 30:933, (1982); Bitter et al., Proc. Natl. Acad. Sci. USA 81:5330, (1984); U.S. Pat. No. 4,546,082; and European published patent application No. 324,274, which are hereby incorporated by reference). Another suitable leader sequence is the S. cerevisiae MF alpha 1 (alpha-factor) is synthesized as a prepro form of 165 amino acids comprising signal-or prepeptide of 19 amino acids followed by a "leader" or propeptide of 64 amino acids, encompassing three N-linked glycosylation sites followed by (LysArg(Asp/Glu, Ala)2-3 alpha-factor)4 (Kurjan, et al., Cell 30:933–43 (1982), which is hereby incorporated by reference). The signal-leader part of the preproMF alpha 1 has been widely employed to obtain synthesis and secretion of heterologous proteins in S. cerivisiae. Use of signal/leader peptides homologous to yeast is known from. U.S. Pat. No. 4,546,082, European Patent Applications Nos. 116,201; 123,294; 123,544; 163,529; and 123,289 and DK Patent Application No. 3614/83, which are hereby incorporated by reference. In European Patent Application No. 123,289, which is hereby incorporated by reference, utilization of the S. cerevisiae a-factor precursor is described whereas WO 84/01153, which is hereby incorporated by reference, indicates utilization of the Saccharomyces cerevisiae invertase signal peptide, and German Patent Application DK 3614/83, which is hereby incorporated by reference, indicates utilization of the Saccharomyces cerevisiae PH05 signal peptide for secretion of foreign proteins.

The alpha-factor signal-leader from Saccharomyces cerevisiae (MF alpha 1 or MF alpha 2) may also be utilized in the secretion process of expressed heterologous proteins in yeast (U.S. Pat. No. 4,546,082, European Patent Applications Nos. 16,201; 123,294; 123 544; and 163,529, which are hereby incorporated by reference). By fusing a DNA sequence encoding the S. cerevisiea MF alpha 1 signal/leader sequence at the 5' end of the gene for the desired protein secretion and processing of the desired protein was demonstrated. The use of the mouse salivary amylase signal peptide (or a mutant thereof) to provide secretion of heterologous proteins expressed in yeast has been described in Published PCT Applications Nos. WO 89/02463 and WO 90/10075, which are hereby incorporated by reference.

U.S. Pat. No. 5,726,038 describes the use of the signal peptide of the yeast aspartic protease 3, which is capable of providing improved secretion of proteins expressed in yeast. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., Proc. Natl. Acad. Sci. USA 75:1929 (1978), which is hereby incorporated by reference. The Hinnen et al. protocol selects for Trp transformants in a selective medium, wherein the selective medium consists of 0.67% yeast nitrogen base, 0.5% casamino acids, 2% glucose, 10 μg/ml adenine and 20 μg/ml uracil.

The gene may be maintained on stable expression vector, an artificial chromosome, or by integration into the yeast host cell chromosome. Integration into the chromosome may be accomplished by cloning the phytase gene into a vector which will recombine into a yeast chromosome. Suitable vectors may include nucleotide sequences which are homologous to nucleotide sequences in the yeast chromosome. Alternatively, the phytase gene may be located between recombination sites, such as transposable elements, which can mobilize the gene into the chromosome.

The present invention also provides a method of producing phytase by providing an isolated appA gene, which encodes a protein or polypeptide with phytase activity, and expressing the gene in host cell. Preferably the appA gene is isolated from Escherichia coli. Preferred host cells include yeast or filamentous fungi. The preferred filamentous fungi is Aspergillus niger and the preferred yeast are Saccharomyces, Kluyveromyces, Torulaspora, and Schizosaccharomyces, in particular, the yeast strain, Saccromyces cerivesia.

A method of converting phytate to inositol and inorganic phosphorus is also provided. An appA gene is isolated from an organism, using techniques well known in the art. A protein or polypeptide with phytase activity is then expressed from the gene in a host cell. The resulting protein or polypeptide is mixed or contacted with phytate. This technique is especially useful for treating phytate in food or animal feed.

The preferred appA gene is isolated from Escherichia coli.

While the phytase enzyme produced in a yeast system released phytate-P from corn and soy as effectively as the currently commercial phytase, it appeared to be more thermostable. This phytase overexpression system in yeast can be used to provide thermostable phytase for use in the food and feed industries.

EXAMPLES

Example 1

Materials and Methods for Overexpressing PhyA in E. Coli, S. Lividans, and a Saccharomyces System Phytase gene, host strains, and expression plasmids. Phytase gene, phyA, was kindly provided by Dr. E. J. Mullaney of the USDA. The gene (GenBank Accession number M94550) was contained in plasmid pMD4.21 in E. coli strain HB101. A 2.7 kb SphI fragment of A. niger DNA contained the coding region of the deglycosylated phytase and its 5' and 3' flanking sequences. A plasmid containing the signal peptide sequence, Spxy, of the active xylanase gene of Aureobasidum pullulans (GenBank Accession number U10298) was kindly provided by Dr. X. L. Li of the University of Georgia. The E. coli strain DH5α was used as an initial host for all the recombinant plasmids. In order to express phyA in E. coli, the expression vector, pET25b(+) (Novagen, Madison, Wis.) and the expression host, BL21 (DE3)pLysS, were used. In order to express phyA in S. lividans TK 24, plasmid pSES1 (Jung, E. D. et al., "DNA Sequences and Expression in Streptomyces Lividansoglucanase Gene and an Endoglucanase Gene from Thermomonospora Fusca," Appl. Environ. Microbiol., 59:3032–43 (1993), which is hereby incorporated by reference), was used to construct the shuttle plasmid (from Dr. D. B. Wilson of Cornell University and he obtained it from Dr. D. A. Hopwood, John Innes Institute, Norwich, England). In order to express phyA in yeast, the expression vector pYES2 and the host S. cerevisiae strain, INVSc1 (Invitrogen, San Diego, Calif.) were used.

Plasmid cassette constructions and transformations. All the constructed plasmids and the correspondent hosts are listed in Table 1. A 1.4 kb PCR fragment of phyA gene was amplified from the pMD4.21 by using two primers: upstream 5'-CGG AAT TCG TCA CCT CCG GAC T-3' (SEQ ID NO:1) and downstream 5'-CCC AAG CTT CTA AGC AAA ACA CTC-3' (SEQ ID NO:2). The resulting fragment contained the sequence coding for the deglycosylated phytase of A. niger, PhyA, and EcoRI and HindIII restriction site upstream and downstream, respectively. After purification with Geneclean II kit (Bio101, Inc., La Jolla, Calif.), the fragment was inserted into pET25b(+), and the resulting construct pEP1 (6893 bp) was transformed into BL21(DE3)pLysS after initial confirmation in DH5α cells. The expression was under the control of T7 promoter followed by the lead sequence (pel B) encoding 21 amino acids, and phyA. The host transformed with the pET25(+) vector only was used as the control.

TABLE 1

Expression vectors, constructs, and their host strains used in the study

| Plasmid | Host | Description[1] | Reference[2] |
|---|---|---|---|
| pET25b(+) | E. coli DH5α and BL21 (DE3)pLysS | Expression vector | Novagen |
| pEP1 | E. coli BL21 (DE3)pLysS | pET25bα(+) + phyA gene | This paper |
| PSES2 | E. coli DH5α and S. lividans TK24 | Expression vector | Jung et al.[2], 1993 |
| PSPP1 | E. coli DH5α and S. lividans TK24 | pSES2 + Spe2 + phyA | This paper |
| PYES2 | E. coli DH5α and S. cerevisiae INVSc1 | Expression vector | Invitrogen |
| PYEP1 | E. coli DH5α and S. cerevisiae INVSc1 | pYES2 + Spe2 + phyA | This paper |
| PYXP1 | E. coli DH5α and S. cerevisiae INVSc1 | pYES2 + Spxy + phyA | This paper |
| PYPP1 | E. coli DH5α and S. cerevisiae INVSc1 | pYES2 + Sphy + phyA | This paper |

[1]Spe2 is the signal peptide for endoglucanase E2 of T. fusca (Wilson, D. B., "Biochemistry and Genetics of Actinomycete Cellulases," Crit. Rev. Biotechnol, 12: 45–63 (1992), which is hereby incorporated by reference); Spxy is the signal peptide for xylanase of A. pullulans (Liand Ljungdahl, "Cloning, Sequencing, and Regulation of a Xylanase Gene fromthe Fungus Aureobasidium pullulans Y-2331-1," Appl. Environ. Microbiol., 60: 3160–66 (1994); Li and Ljungdahl, "Expression of Aureobasidium pullulans xynA in, and Secretion of the Xylanase from, Saccharomyces cerevisiae," Appl. Environ. Microbiol., 62: 209–13 (1996),which are hereby incorporated by reference); and Sphy is the signal peptide for phyA of A. niger (Hartingsveldt et al., "Cloning, Characterization and Overexpression of the Phytase-Encoding Gene (phyA) of Aspergillus Niger," Gene 127: 87–94 (1993), which is hereby incorporated by reference).
[2]Jung, E. D. et al., "DNA Sequences and Expression in Streptomyces Lividansoglucanase Gene and an Endoglucanase Gene from Thermomonospora Fusca," Appl. Environ. Microbiol., 59: 3032–43 (1993), which is hereby incorporated by reference).

The construction of the plasmid for phyA expression in S. lividans started with the synthesis of a fragment containing pLT1 promoter and Spe2 signal peptide (Lao, G. et al., "DNA Sequences of Three Beta-1,4-endoglucanase Genes From Thermomonospora Fusca," J. Bacteriol., 173:3397–407 (1991), which is hereby incorporated by reference) by PCR. An upstream primer, 5'-CAG CTA TGA CCA TGA TTA CGC C-3' (SEQ ID NO:3), and a downstream primer, 5'-CCT AGA ACG GGA ATT CAT TGG CCG CC-3' (SEQ ID NO:4), contained PstI and EcoRI restriction sites, respectively. The fragment was amplified from pBW2 (Jung, E. D. et al., "DNA Sequences and Expression in Streptomyces Lividans of an Exoglucanase Gene and an Endoglucanase Gene From Thermomonospora Fusca," Appl. Environ. Microbiol., 59:3032–43 (1993), which is hereby incorporated by reference) and then digested with PstI and EcoRI, while the construct pEP1 and plasmid pBluescript SK+ (Strategene, La Jolla, Calif.) were digested with EcoRI and HindIII, and PstI and HindIII, respectively. The three digested fragments were subsequently purified using Geneclean II kit and ligated into a single recombinant construct that contained the desired restriction sites of PstI and KpnI (from pBluescript SK*), pLT1 promoter and Spe2 leading peptide of endoglucanase E2 (551 bp, Lao, G. et al., "DNA Sequences of Three Beta-1,4-endoglucanase Genes From Thermomonospora Fusca," J. Bacteriol., 173:3397–407 (1991), which is hereby incorporated by reference), and phyA gene (1365 bp). After the construct was digested with PstI and KpnI, the resulting fragment was inserted into the expression vector pSES1, and the formed shuttle plasmid (pSPP1, 9131 bp) was transformed into the host S. lividans protoplasts according to Hopwood et al. (Hopwood, D. A., et al., Genetic Manipulation of Streptomyces—A Laboratory Manual, The John Innes Foundation, Norwich, England (1985), which is hereby incorporated by reference). Likewise, a control was prepared by transforming S. lividans with expression vector pSES2.

Three shuttle plasmids with three different signal peptide sequences were constructed to express phyA in the yeast system (See Table 2). The first plasmid was originated from a HindIII digested fragment of pSPp1, including the promoter pLT1, lead sequence Spe2, and the coding region sequence of phyA. The fragment was ligated into the HindIII site of pYES2 treated with calf intestinal alkaline phosphatase and the plasmid was named pYEP1 (7783 bp) after its right orientation was confirmed. The second plasmid contained Spxy, a signal peptide sequence of xylanase gene from A. pullulans (Li, X. L. et al., "Cloning, Sequencing, and Regulation of a Xylanase Gene From the Fungus Aureobasidium Pullulans) Y-2311-1," Appl. Environ. Microbiol., 60:3160–166 (1994); Li, X. L. et al., "Expression of Aureobasidium Pullulans XynA in, and Secretion of the Xylanase From, Saccharomyces Cerevisiae a," Appl. Environ. Microbiol., 62:209–13 (1996), which are hereby incorporated by reference), and phyA gene. Spxy was spliced with phyA by overlap extension (Horton, R. M., "In Vitro Recombination and Mutagenesis of DNA: SOEing Together Tailor-Made Genes," PCR Protocols: Current Methods and Applications, 251–61 (1993), which is hereby incorporated by reference) with two successive steps of PCR. One was to amplify Spxy sequence from pCE4 (Li, X. L. et al., "Expression of Aureobasidium Pullulans XynA in, and Secretion of the Xylanase From, Saccharomyces Cerevisiae a," Appl. Environ. Microbiol., 62:209–13 (1996), which is hereby incorporated by reference) using upstream primer (5'-CCC AAG CTT GAT CAC ATC CAT TCA-3') (SEQ ID NO:5) with a HindIII restriction site (primer 1) and overlapping downstream primer (5'-CGG GGA CTG CTA GCG CAC GTT CGA T-3', primer 2) (SEQ ID NO:6). The other PCR was to amplify the coding region of phyA from pEP1 using overlapping upstream primer (5'-ATC GAA CGT GCG CTA GCA GCA GTC CCC G-3', primer 3) (SEQ ID NO:7) and downstream primer (5'-GCT CTA GAC TAA GCA AAA CAC TCC-3', primer 4) (SEQ ID NO:8) with a XbaI restriction site. The second step of PCR was conducted to merge the two fragments generated from the above two PCR by using the two purified fragments as the templates and primers 1 and 4. The resulting fragment contained HindIII and XbaI restriction sites and was cloned into pSES2. This plasmid was named pYXP1 (7219 bp). The third plasmid contained the signal peptide (Sphy) sequence of phyA and the coding region of phyA, excluding the intron between them (Hartingsveldt, W. van., et al., "Cloning, Characterization and Overexpression of the Phytase-Encoding Gene (phyA) of *Aspergillus Niger,*" *Gene* 127:87–94 (1993), which is hereby incorporated by reference). Two primers, including a 70 bp of upstream primer contained the signal peptide with an engineered KpnI restriction site and a downstream primer that was the same one used for pYXP1 construction (primer 4) were used to amplify the desired fragment from pEP1. The PCR product was digested with KpnI and XbaI and cloned into pSES2, resulting in a plasmid named pYPP1 (7176 bp). All the above three constructs were transformed into *S. cerevisiae* by the method of Ito et al., "Transformation of Intact Yeast Cells Treated with Alkali Cations," *J. Bacteriol.,* 153:163–68 (1983), which is hereby incorporated by reference.

TABLE 2

Signal peptides used for expression of phyA in S. cerevisiae

| Construct Size (bp) | Peptide | Gene | Organism | Phytase activity[1] (mPU/ml) |
|---|---|---|---|---|
| pYEP1 7783 | Spe2 (93 bp) | Cellulase E2 | *T. fusca* | .80 |
| pYXP1 7219 | Spxy (102 bp) | Xylanase A | *A. pullulans* | Non-detectable |
| pYPP1 7176 | Sphy (57 bp) | PhyA Phytase | *A. niger* | 146 |
| pSES1[2] 7224 | | | *S. cerevisiae* | Non-detectable |

[1]The phytase activity was detected in the supernatant of cell culture of Sabouraud-raffinose medium 15 hours after induced by adding galactose. See text for definition of phytase units.
[2]Expression vector for *S. cerevisiae*, used as a control.

Growth medium and induction of the gene expression. In the *E. coli* system, the transformants were grown in 50 ml of LB medium containing 50 μg/ml of ampicillin at 30° C. After the $OD_{600}$ value of the medium reached 0.5 to 0.6, phytase gene expression was induced by adding IPTG (isopropyl b-D-thiogalactopyranoside) into the medium to a final concentration of 1 mM. Three hours after the induction, cells were collected by spinning down at 8000×g for 15 minutes, washed with 1×PBS, and lysed by lysozyme. Soluble and insoluble fractions of the cells were prepared, and a sample containing 500 μg of total protein (Lowry, O. H. et al., "Protein Measurement With the Folin Phenol Reagent," *J. Biol. Chem.,* 193:265–75 (1951), which is hereby incorporated by reference) was suspended in the same volume of 2×SDS buffer and analyzed by SDS-PAGE (Laemmli, U. K., "Cleavage of Structural Proteins During the Assembly of the Head of Bacteriophage T4," *Nature* (London), 227:680–85 (1970), which is hereby incorporated by reference).

Recombinant *S. lividans* was grown in TSB broth with 5 μg/ml of *thiostrepton* at 30° C. (Jung, E. D. et al., "DNA Sequences and Expression in *Streptomyces Lividans* of an Exoglucanase Gene and an Endoglucanase Gene from *Thermomonospora Fusca,*" *Appl. Environ. Microbiol.,* 59:3032–43 (1993), which is hereby incorporated by reference). After 72 hours incubation, the cells and medium were harvested and prepared for SDS-PAGE (Wilson, D. B., "Biochemistry and Genetics of Actinomycete Cellulases," *Crit. Rev. Biotechnol.,* 12:45–63 (1992), which is hereby incorporated by reference).

Transformants of *S. cerevisiae* were initially grown in Sabouraud-raffinose (4%) medium (100 ml) without uracil for 48 hours, sterile galactose was then added into the medium (2%) to induce phytase expression. Samples of media and cells were collected at various time points, and extracellular and intracellular samples were prepared as described by Li and Ljungdahl, "Expression of *Aureobasidium pullulans* xynA in, and Secretion of the Xylanase from, *Saccharomyces cerevisiae,*" *Appl. Environ. Microbiol.,* 62:209–13 (1996), which is hereby incorporated by reference. When needed, the supernatant of the expressed cell culture fractions was concentrated with Stirred Cells of Amicon (Beverly, Mass.) by using YM10 membranes (MW cutoff of 10,000). Other media were tested accordingly.

Enzyme protein and activity assay. Amounts of expressed phytase protein under various conditions were quantified by the relative densitometry of specific bands in SDS-PAGE, using IS-1000 Digital Imaging System (Alpha Innotech Corporation, San Leandro, Calif.). Phytase activity in the samples of media and cells was determined as previously described (Piddington, C. S. et al., "The Cloning and Sequencing of the Genes Encoding Phytase (phy) and pH 2.5-optimum Acid Phosphatase (aph) from *Aspergillus niger* var. *awamori,*" *Gene,* 133:56–62 (1993), which is hereby incorporated by reference) and the inorganic phosphate released was assayed by the method of Chen, P. S. et al., "Microdetermination of P," *Anal. Chem.,* 28:1756–58 (1956), which is hereby incorporated by reference. One phytase unit (PU) was defined as the amount of enzyme that releases one pmol of inorganic phosphate from sodium phytate per minute at 37° C.

Western blotting (immunoblot) analysis. The soluble fraction of the cell mass of the phytase transformed *E. coli* and the medium supernatant of *S. lividans* and *S. cerevisiae* transformants were collected as for SDS-PAGE. After electrophoresis, the proteins were then transferred onto Protran® nitrocellulose membrane (Schleicher & Schuell, Keene, N.H., USA) in 20 mM Tris-HCl (pH 8.3), 20% methanol, and 0.1% SDS, by using a Mini Trans-Blot cell (Bio-Rad Laboratories). Transfer was done overnight at a constant 50 V and the initial buffer temperature was 4° C. The membranes were then subjected to Western blot analysis. A rabbit polyclonal IgG (Kindly provided by Dr. A. H. J. Ullah of USDA. Dilution, 1: 5,000) against purified native *A. niger* phytase was used as the first antibody. The blotting was finalized using Immuno-Blot Assay Kit (Bio-Rad Laboratories) containing a second antibody conjugated with horseradish peroxidase.

Total RNA isolation and analysis. Total RNA was isolated with TRIzol™ Reagent (GIBCO BRL, Gaithersburg, Md.) from *E. coli* and *S. cerevisiae* transformants 3 and 15 hours after induction, respectively. RNA samples (10 μg per lane) were then separated by formaldehyde agarose (1.5%, wt/vol) gel electrophoresis and transferred to Hyblot membranes (National Labnet, Woodbridge, N.J.) (Davis et al., *Basic Methods in Molecular Biology,* 2nd Ed., Appleton and Lange, Norwalle, Conn. (1994), which is hereby incorporated by reference). A 1.4 kb EcoRI-HindIII fragment in plasmid pEP1 was prepared and was random-primed labeled with $^{32}P$ using a DNA labeling kit followed by G-50 column purification (Pharmacia Biotech., Piscataway, N.J.) and then hybridized with the blotted RNA membranes in a hybridization oven (Hybaid, Middlesex, UK). The hybridized membranes were exposed to screens in Fuji Imaging Plate and analyzed by Bio-Imaging Analyzer (Kohshin Graphic Systems, Fuji, Japan).

Example 2

Expression of PhyA in *E. coli*

Figure 2:
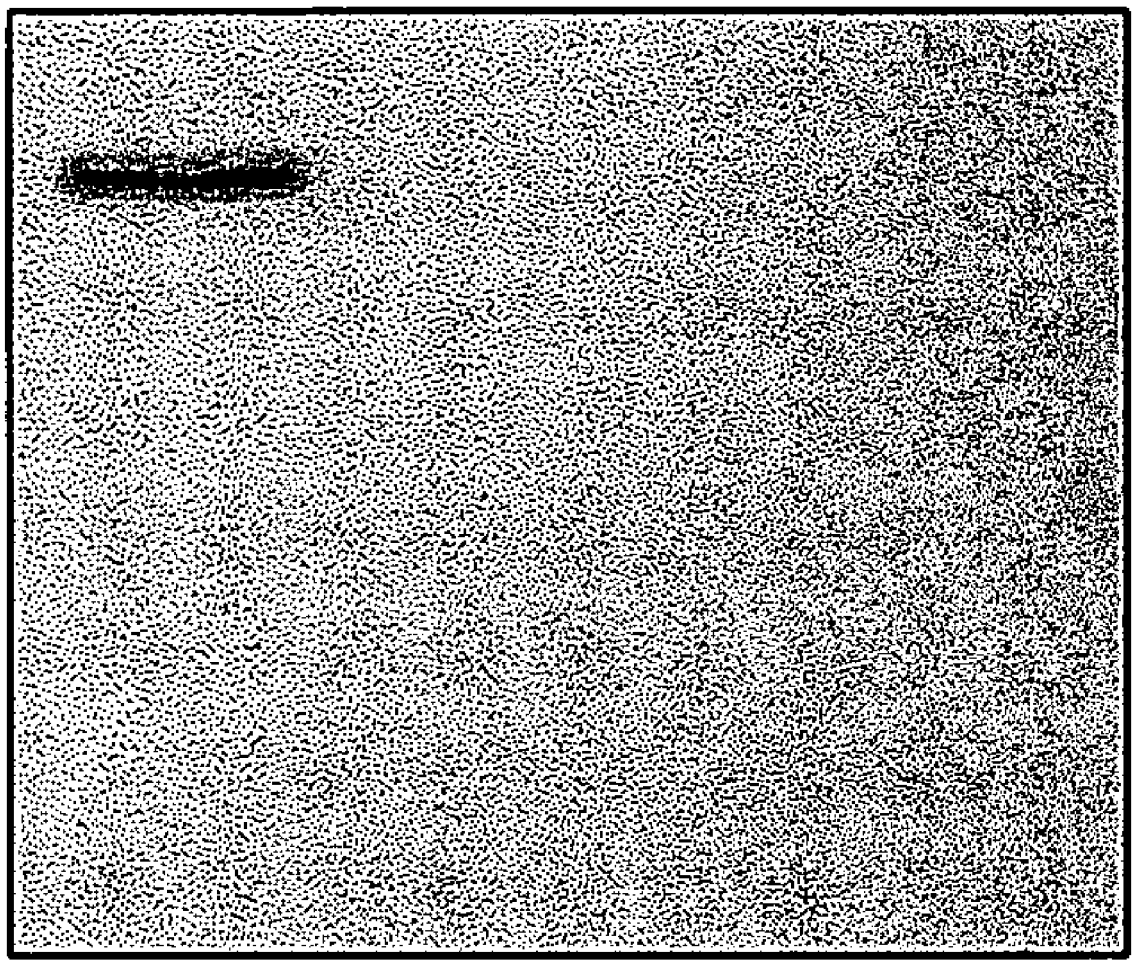
FIG. 2 shows the Western blot analysis of the expressed phytase protein in *E. coli*. The antibody was raised against purified native phytase of *A. niger*. Each lane contained 50 μg total intracellular protein. Lanes 1 and 2: Recombinants after and before induction. Lanes 3 and 4: control (only the expressing vector) after and before induction.
Figure 3:
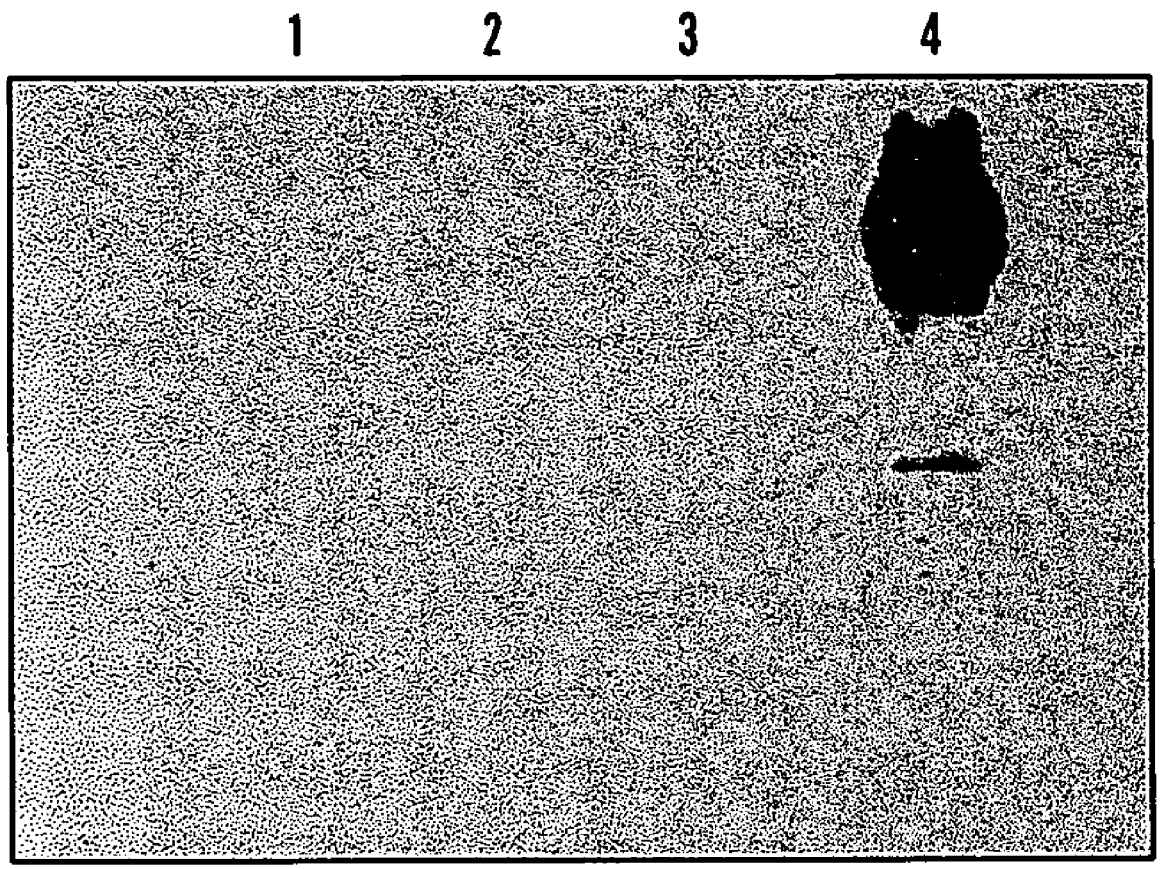
FIG. 3 is a scan image of Northern blotting analysis of the mRNA of PhyA in *E. coli*. A 1.4 kb PhyA probe was used. Each lane contained 20 μg of total RNA. Lanes 1 and 2: RNA isolated from the control cells (only the expression vector) before and after induction. Lanes 3 and 4: RNA isolated from the recombinants containing PhyA before and after induction.

Four hours after the induction, a specific band (~55 kDa) was viewed in SDS-PAGE (12.5%) of the soluble cell fraction, compared to the only expression vector transformed control (See FIGS. 1 and 2). This band represented 3.8% of the total soluble protein of this fraction. Correspondingly, northern analysis showed overexpression of phyA mRNA in these phytase gene transformants and no signal was viewed in the control cells (See FIG. 3).

Figure 4:
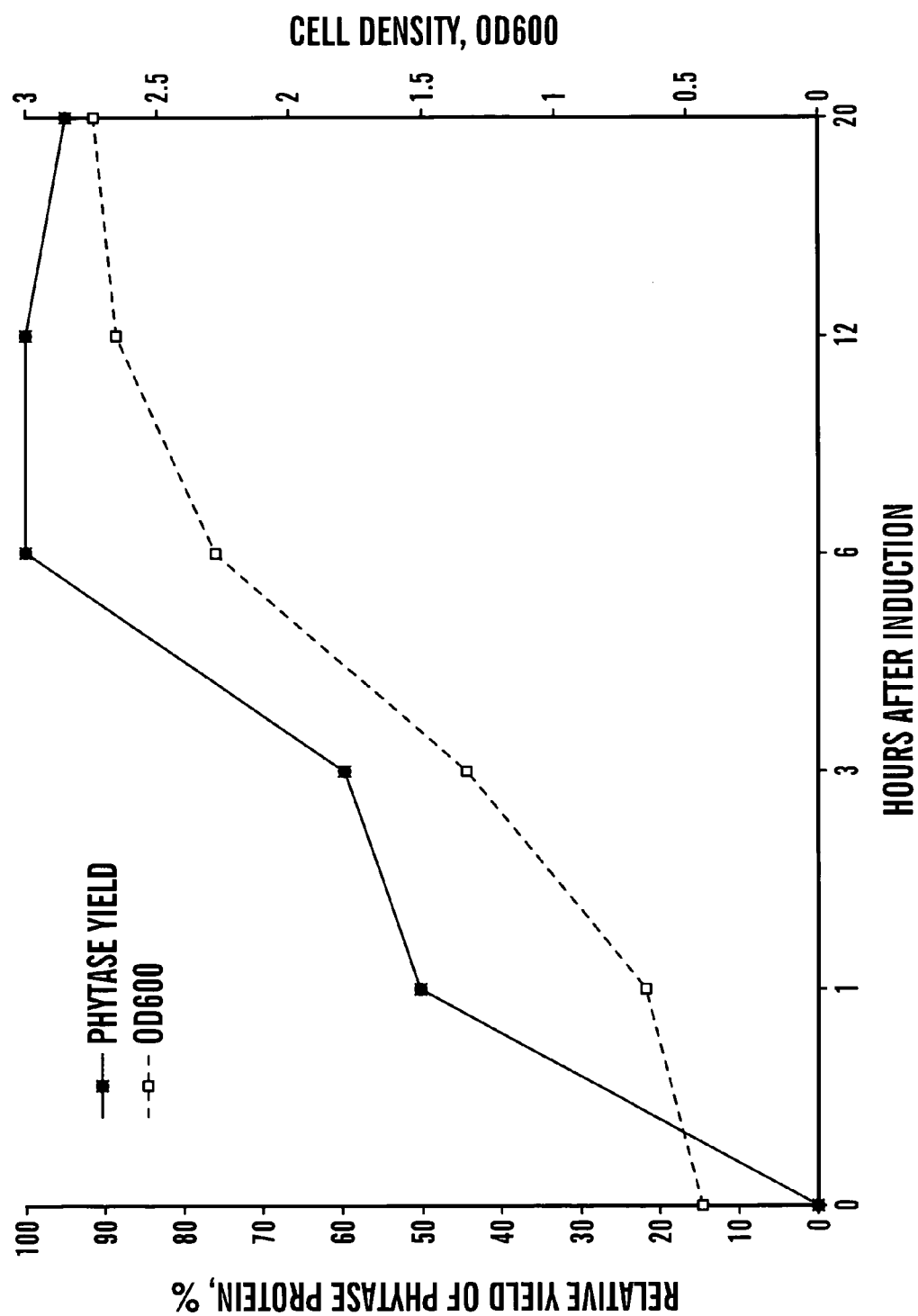
FIG. 4 is a time course of the induced expression of phytase (pEP1) in *E. coli* BL21(DE3). The cells were induced when the $OD_{600}$ reached 0.5. The soluble protein, prepared at each time point, was quantified by SDS-PAGE analysis.

In order to optimize phytase protein expression, the time course and the effects of a series of factors on the expression were studied. These factors included incubation temperature (30 and 37° C.), medium pH (4.0, 5.0, 6.0, 7.0, 8.0, and 9.0), anaerobiosis (adding sterile mineral oil on the top of the growing cells), inorganic phosphate level in the medium (Dassa, E. et al., "The Acid Phosphatases with Optimum pH of 2.5 of *Escherichia coli*," *J. Bio. Chem.*, 257:6669–76 (1982), which is hereby incorporated by reference), and sodium phytate (0, 0.1, 0.2, 0.3, 0.4, and 0.5 mM). Results indicated that expression of phytase protein was accumulated linearly with time for the first six hours after induction (See FIG. 4). Thereafter, the expression remained relatively unchanged although bacterial cells continued to grow. Only medium pH and sodium phytate concentration significantly affected the phytase protein expression. Maximum protein was shown at pH 6.0 and 0.3 mM of sodium phytate, in which phytase protein was increased from 3.8 to 9.6% of the total soluble protein.

No phytase activity was detected extracellularly or intracellularly. This may not be completely unexpected, because the native phytase from *A. niger* is a glycoprotein with a size of 70–80 kDa (Hartingsveldt et al., "Cloning, Characterization and Overexpression of the Phytase-Encoding Gene (phyA) of *Aspergillus Niger*," *Gene* 127:87–94 (1993), which is hereby incorporated by reference). The protein expressed in the *E. coli* system of this study had a size of approximately 55 kDa. Presumably, the lack of glycosylation of the protein and other necessary post-translational modifications during secretion would preclude phytase activity.

Example 3

Expression of PhyA in *S. lividans*

Figure 5:
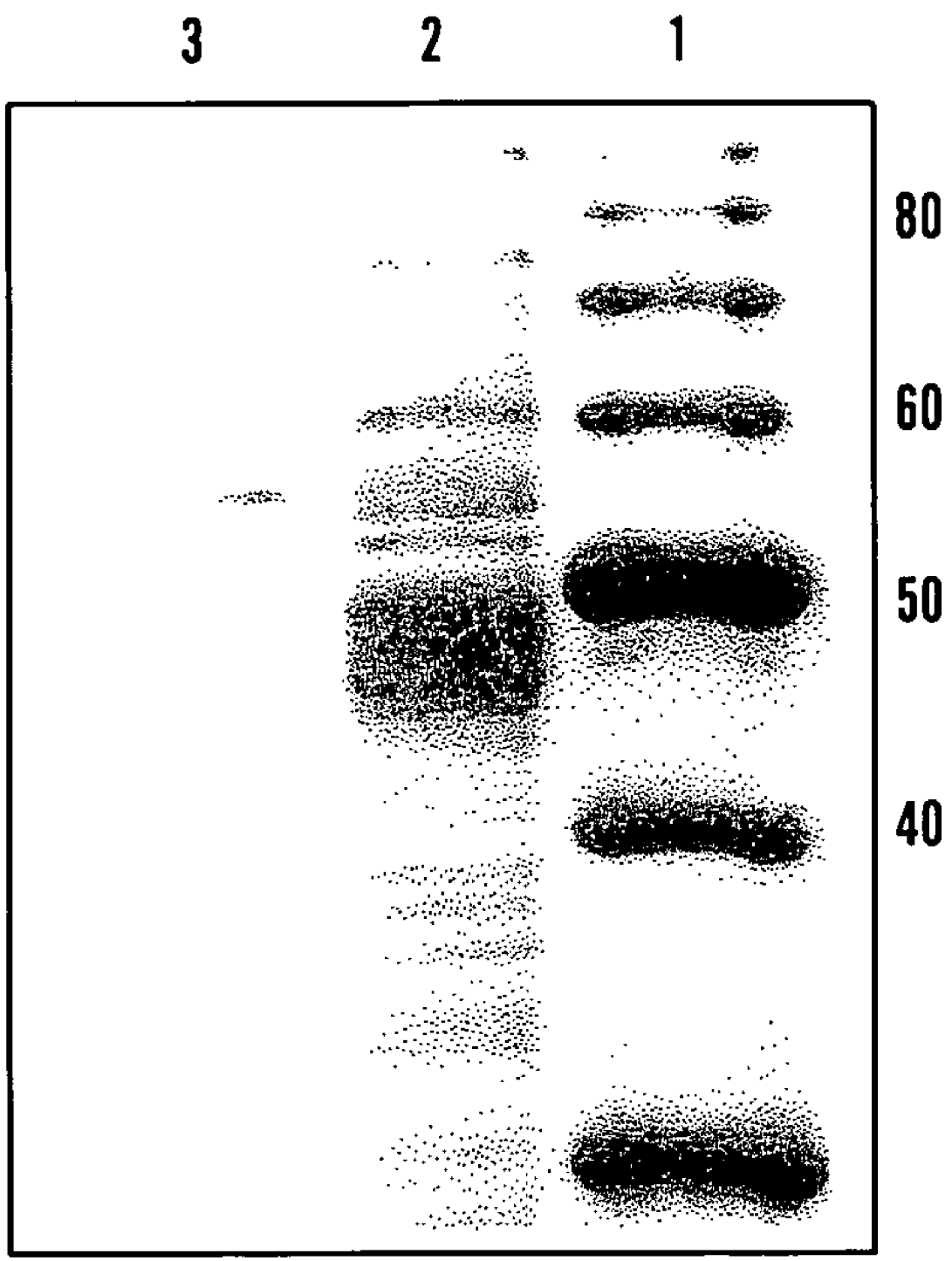
FIG. 5 shows an SDS-PAGE analysis of the expressed extracellular phytase protein by the phytase transformed *S. lividans* after growing for 72 hours. Cells were spun for 15 minutes at 8,000×g, and the supernatant was subjected to gel electrophoresis. Lane 1: Marker; Lane 2: Control with the only expression vector; Lane 3: Positive colony expressed phytase and the size was approximately 57 kDa.
Figure 6:
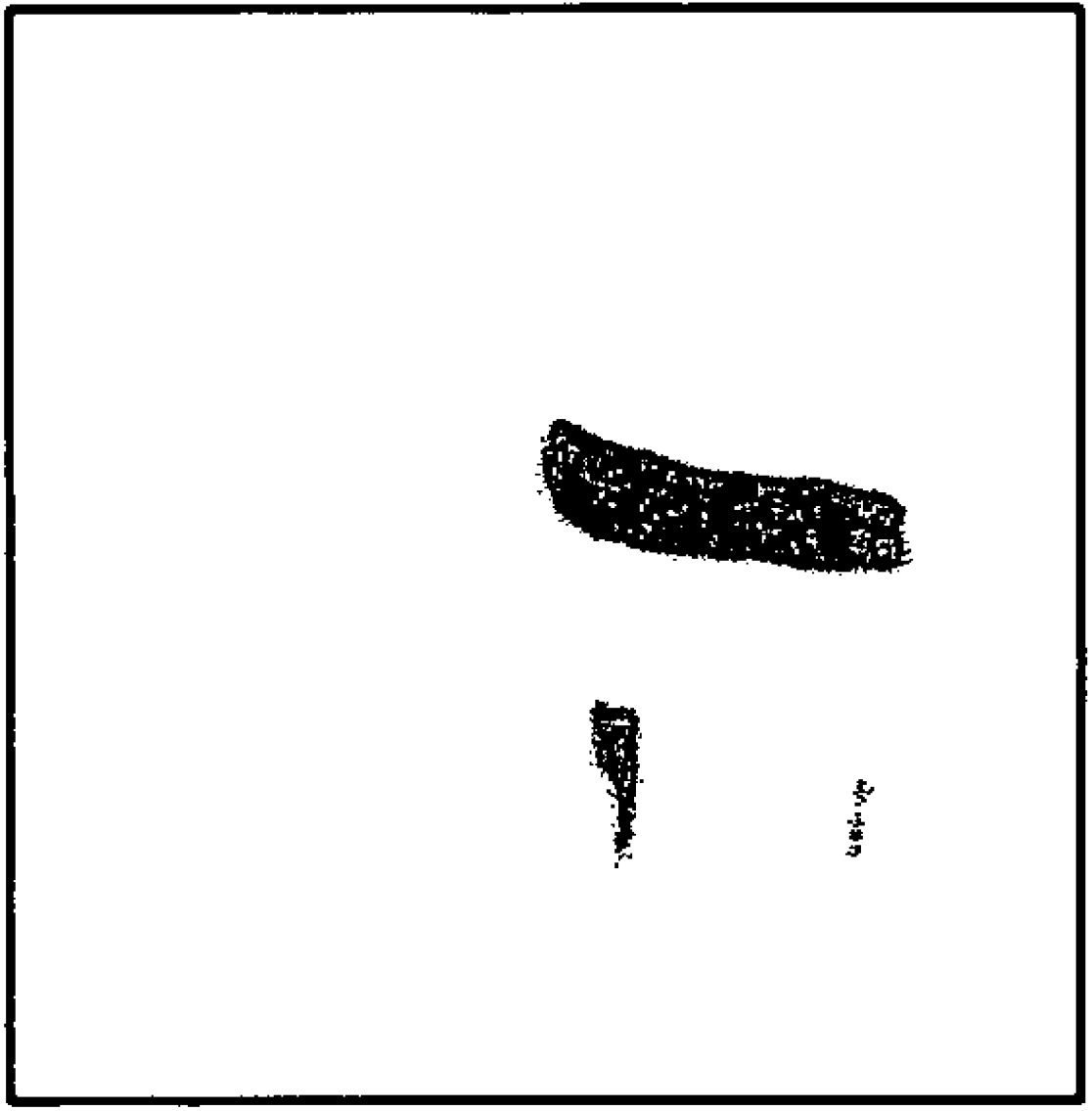
FIG. 6 shows the Western blot analysis of the phytase expressed by *S. lividans*, using a phytase antibody raised against purified native phytase of *A. niger*. Each lane was loaded with 20 μg medium (supernatant) protein. Lane 1: Supernatant from the vector transformed control cell culture; Lane 2: Supernatant from the culture inoculated with the positive colony.

Heterologous genes have been expressed in *S. lividans*, and the resulting products secreted into the medium with enzymatic activity (Ghangas, G. S. et al., "Cloning of the *Thermomonospora Fusca* Endoglucanase E2 Gene in *Streptomyces Lividans*: Affinity Purification and Functional Domains of the Cloned Gene Product," *Appl. Environ. Microbiol.*, 54:2521–26 (1988); Wilson, D. B., "Biochemistry and Genetics of Actinomycete Cellulases," *Crit. Rev. Biotechnol.*, 12:45–63 (1992); Jung, E. D. et al., "DNA Sequences and Expression in *Streptomyces Lividans* of an Exoglucanase Gene and an Endoglucanase Gene from *Thermomonospora Fusca*," *Environ. Microbiol.*, 59:3032–43 (1993), which are hereby incorporated by reference). Similarly, phyA gene was expressed in *S. lividans* and the protein was introduced into the medium, as shown in a specific band in the SDS-PAGE analyzed medium samples (See FIGS. 5 and 6). This suggested that the signal peptide from endoglucanase E2 gene of *T. fisca* was able to lead phytase protein out of the cell. This protein was 57 kDa and represented 16.2% of the total protein in the medium. Changing medium pH to 6.0 and adding 0.3 mM of sodium phytate in the medium improved the protein yield to 20.3% of the total protein. Because phytase protein was secreted into the medium in such a high level, it should be easy to purify and used effectively for a variety of purposes such as producing phytase antibody. Once again, no increased phytase activity was found either in the medium or in the lysed cells. Although the protein size increased a little bit (2–3%) compared to the one expressed in *E. coli*, presumably due to glycosylation of phytase protein in this expression system, there was still no phytase activity.

Example 4

Expression of PhyA in *S. cerevisiae*

Figure 7:
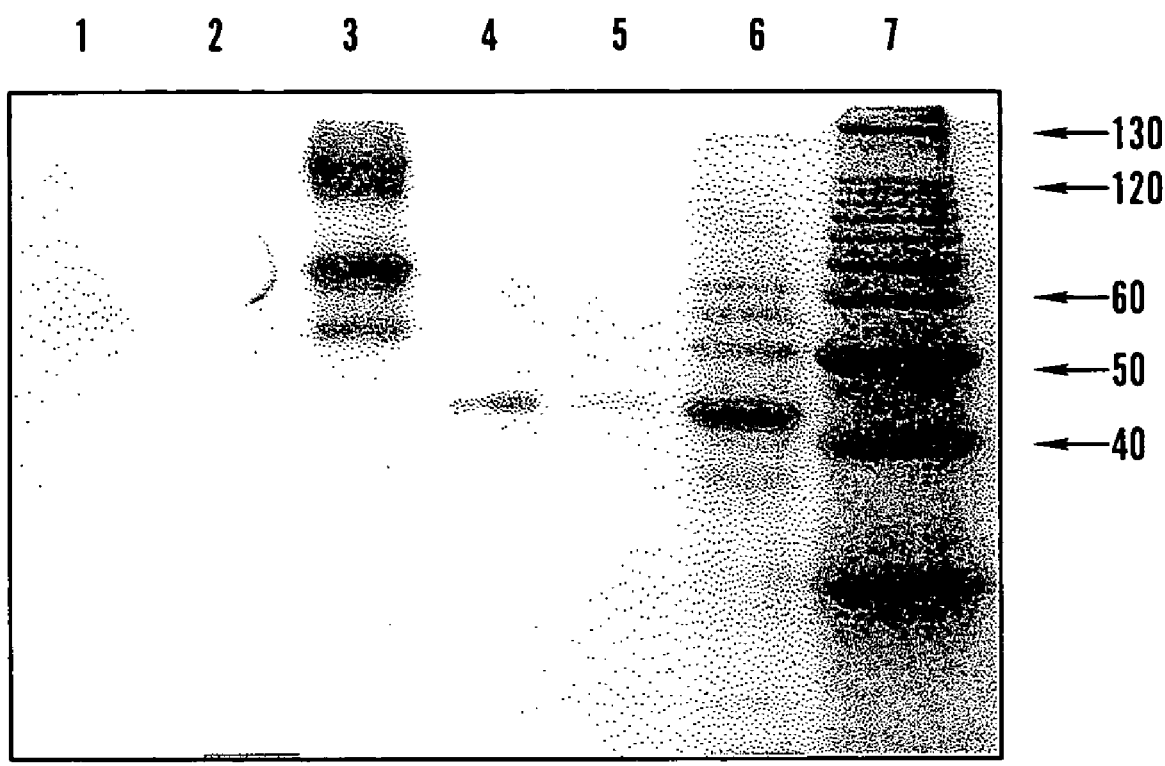
FIG. 7 depicts an SDS-PAGE analysis of the extracellular phytase expressed by *S. cerevisiae*. Each lane was loaded with 50 μg medium (supernatant) protein. Lanes 1 to 3: Supernatant from the culture inoculated with the positive colony harvested at 5, 10, and 25 hours after induction, respectively; Lanes 4 to 6: Supernatant from the vector-transformed control cell culture harvested at 5, 10, and 25 hours after induction, respectively; Lane 7: Marker (kDa). The expressed phytase was approximately 110 kDa (confirmed by Western blot).

Three different signal peptides were used to compare the efficiency in leading the expressed protein out of the cells (See Table 2). The phytase activity was substantially increased in the Sabouraud-raffinose medium growing the transformants of pYEP1 and pYPP1, but not pYXP1. Visible phytase protein was shown by SDS-PAGE 20 hours after induction (FIG. 7).

Figure 8:
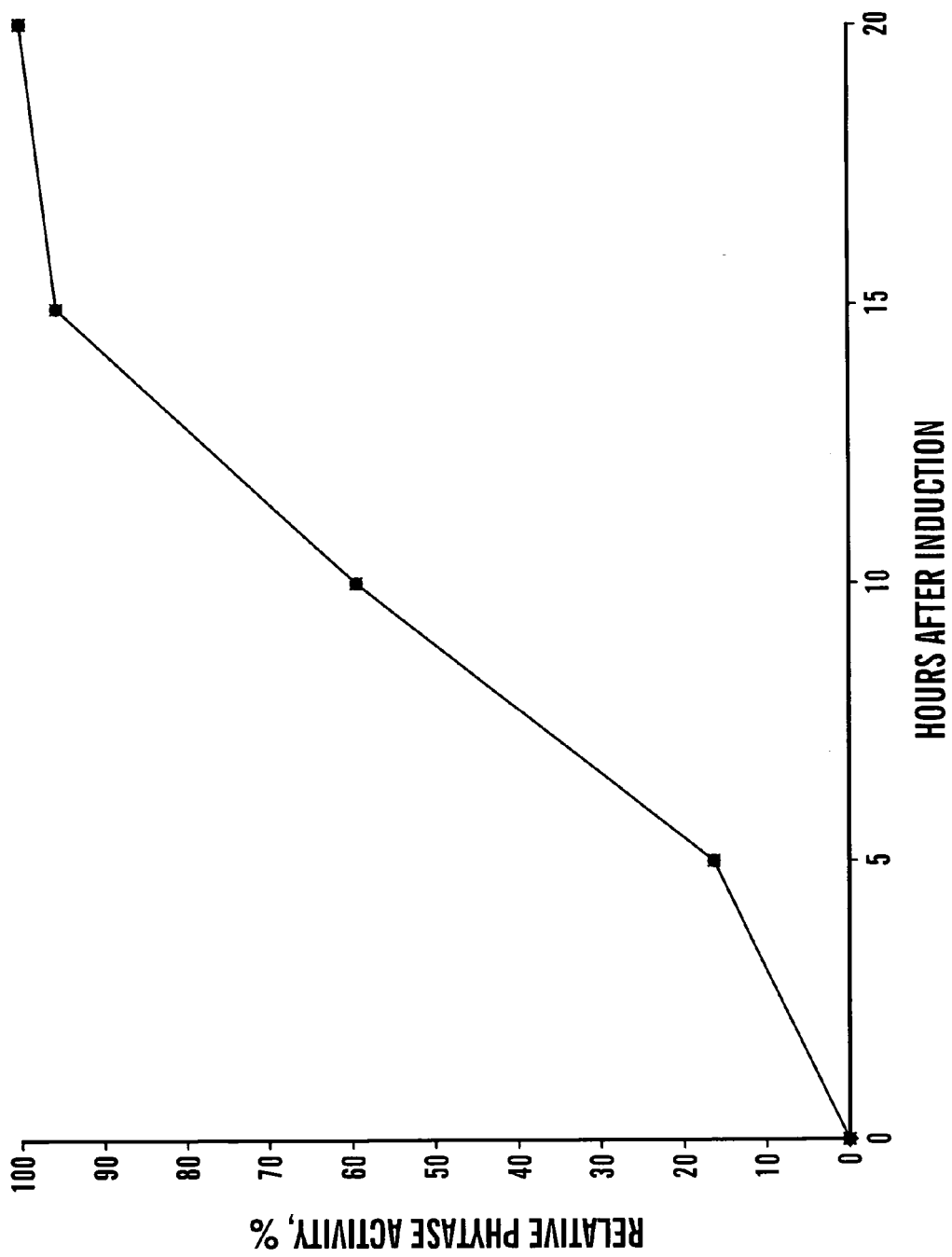
FIG. 8 is a time course of the extracellular phytase activity expressed by the pYPP1 construct transformed *S. cerevisiae* after induced by galactose. The activity was analyzed in the supernatant of the collected medium.

The expression of transformants of pYEP1 and pYPP1 were determined in three different types of medium: Sabouraud-raffinose (Li, X. L. et al., "Expression of *Aureobasidium Pullulans* XynA in, and Secretion of the Xylanase From, *Saccharomyces Cerevisiae*," *Appl. Environ. Microbiol.*, 62:209–13 (1996), which is hereby incorporated by reference), Sabouraud-glycerol, and a modified general-purposed YEPD medium. As to transformants of pYEP1, similar phytase activity was expressed in the Sabouraud-raffinose and Sabouraud-medium, but there was no activity detected in the YEPD medium. In contrast, phytase activity in the medium cultured with transformants of pYPP1 varied greatly with the different types of medium. The activity was enhanced to 375 mU/ml when Sabouraud-glycerol medium was used. The activity was further increased to 1675 mU/ml, when the medium was changed to YEPD (See Table 3). While the YEPD medium was much cheaper than the Sabouraud-raffinose medium, the phytase yield was increased more than ten-folds. Thus, the putative signal peptide from the fungal phytase gene achieved the most efficient expression of the extracellular phytase activity. Nearly all the protein produced was secreted into the YEPD medium, because very little activity was detected in the yeast cells. The time course of the phytase expression in this system was shown in FIG. 8.

TABLE 3

Phytase activity expressed from transformant with pYPP1 in different media

| Medium | Hours after induction (mPU/ml)[1] | | |
|---|---|---|---|
| | 0 | 10 | 15 |
| Sabouraud-raffinose | 22 | 136 | 146 |
| Sabouraud-glycerol | 6 | 174 | 375 |
| YEPD | 18 | 1238 | 1675 |

[1]The phytase activity was detected in the supernatant of cell culture of the three media 0, 10, and 15 hours after induced by adding galactose. See text for definition of phytase units.

A variety of microorganisms including bacilli, yeasts, and filamentous fungi have phytase activity, while *A. niger* NRRL3135 strain produces the highest activity (340 mU/ml, Shieh, T. R. et al., "Survey of Microorganisms for the Production of Extracellular Phytase," *Appl. Environ. Microbiol.*, 16:1348–51 (1968), which is hereby incorporated by reference). *Schwanniomyces castellii* CBS 2863 has the highest phytase activity among 21 yeast strains (140 mU/ml, Lambrechts, C. et al., "Utilization of Phytate by Some Yeasts," *Biotechnology Letters*, 14:61–6 (1992), which is hereby incorporated by reference). Clearly, the recombinant yeast strain transformed with pYPP1 in the present study produced much higher phytase activity (1675 mU/ml) than *A. niger* (4-fold) and *S. castellii* CBS 2863 (11-fold). Maximum phytase production can be obtained in the system by optimizing the incubation conditions and modifying the plasmid cassettes (Demolder, J. W. et al., "Efficient Synthesis of Secreted Murine Interleukin-2 by *Saccharomyces*

Cerevisiae: Influence of 3'-Untranslated Regions and Codon Usage," *Gene,* 111:207–13 (1992), which is hereby incorporated by reference).

Figure 9:
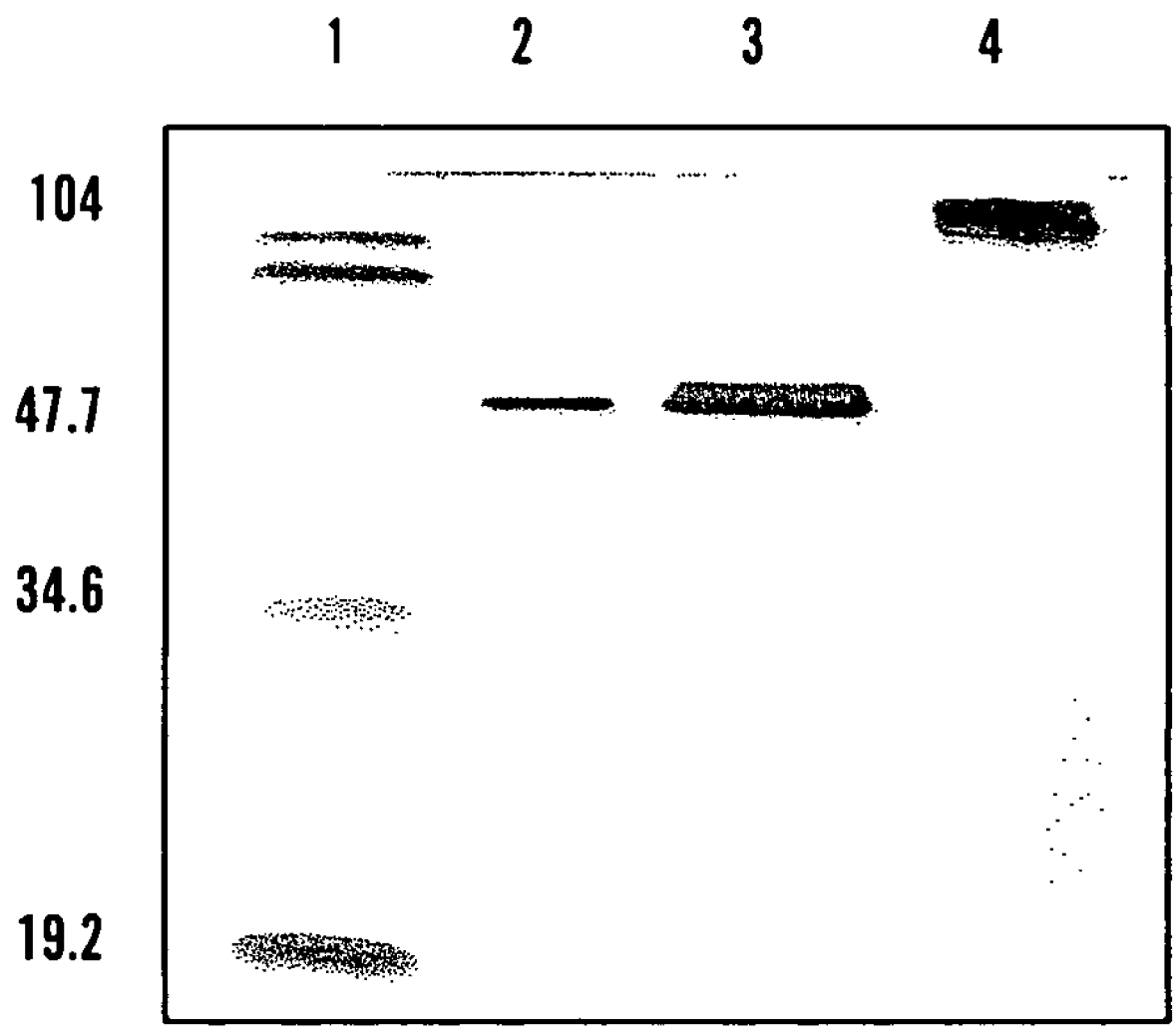
FIG. 9 shows the Western blot analysis of the extracellular phytase expressed by *S. cerevisiae* before and after deglycosylation (Endo H), using a phytase antibody raised against purified native phytase in *A. niger*. Lane 1: Prestained SDS-PAGE standards (kDa) from Bio-Rad; Lanes 2 and 3: deglycosylated 10 and 20 μg phytase protein, respectively; Lane 4: glycosylated phytase (20 μg protein).
Figure 10:
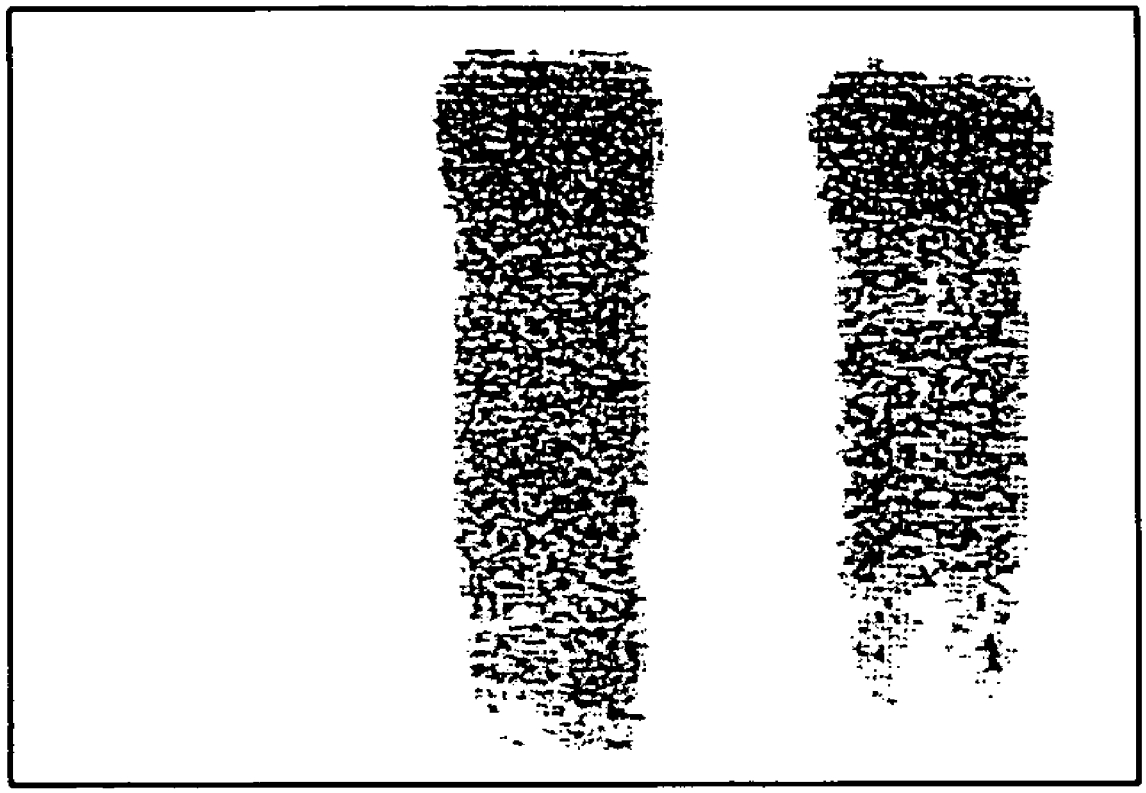
FIG. 10 is a scan image of Northern blot analysis for total RNA isolated from transformed *S. cerevisiae* cells. Lane 1: Control (with only the expression vector pYES2); Lanes 2 and 3: Tranformants of pYPP1.

The high level of phytase activity expression in *S. cerevisiae* was most likely due to the sufficient glycosylation of phytase protein and other post-translational modifications by yeast. After the medium supernatant was concentrated and subjected to SDS-PAGE analysis, there was a band with approximately 110 kDa (See FIGS. 7 and 9), which was larger than the size of the native protein from *A. niger* (Hartingsveldt, W. van. et al., "Cloning, Characterization and Overexpression of the Phytase-Encoding Gene (phyA) of *Aspergillus Niger,*" *Gene* 127:87–94 (1993), which is hereby incorporated by reference). Northern analysis confirmed the specific overexpression of phyA mRNA (See FIG. 10). These results indicated that the yeast system was efficient to overexpress actively extracellular phytase enzyme. Yeast system has several advantages over bacteria or other systems such as *A. niger* (Hartingsveldt, W. van. et al., "Cloning, Characterization and Overexpression of the Phytase-Encoding Gene (phyA) of *Aspergillus Niger,*" *Gene* 127:87–94 (1993), which is hereby incorporated by reference). It carries out post-translational modifications, including proper folding, glycosylation, disulfide bond formation, and proteolysis, during the translocation of proteins through the endoplasmic reticulum and the cell membrane. The secretion of proteins is facilitated by hydrophobic short signal peptides at the N-terminal regions of the protein precursors (Li, X. L. et al., "Expression of *Aureobasidium Pullulans* XynA in, and Secretion of the Xylanase From, *Saccharomyces Cerevisiae*a," *Appl. Environ. Microbiol.,* 62:209–13 (1996), which is hereby incorporated by reference). Proteins secreted by yeast cells are protected from aggregation and protease degradation. Most importantly, enzyme proteins produced by *S. cerevisiae* are easily purified, because it secretes only a few proteins. Considering the well-known safety of yeast products to both human beings and animals, this system is of great potential for human food and animal feed industry.

Example 5

Properties of the PhyA Phytase Overexpressed in *Saccharomyces cerevisiae*

The overexpressed phytase from transformants of pYPP1 plasmid was concentrated and used to study its property (See Table 4). The enzyme showed two optimum pH ranges: 2 to 2.5 and 5.0 to 5.5. However, enzyme activity at pH 2 to 2.5 was only 60% of the activity at pH 5 to 5.5. There was no activity detected at either pH 1 or 8. The optimum pH was virtually the same as the phytase from *A. niger* (Simons et al., "Improvement of Phosphorus Availability by Microbial Phytase in Broilers and Pigs," *Br. J. Nutr.,* 64:525 (1990), which is hereby incorporated by reference), thus active function in hydrolysis of phytate-P in the gastrointestinal tracts would certainly be expected. The optimum temperature of the enzyme was 60° C., while the current one on the market produced by Gist-Brocades is 55° C. (BASF, 1996). More than 80% of the activity remained at 50 to 55° C., but little activity was detected at 75 or 80° C. Heating the enzyme for 15 min at 37 and 80° C., the remaining activity for the expressed yeast phytase of the present invention was 100 and 63%, respectively, and for BASF Gist-Brocades phytase was 100 and 52%, respectively. The differences between the two enzyme sources at any given temperature were significant (See Table 5). Thus, the yeast phytase appeared to be more heat stable than the current commercial phytase product.

TABLE 4

Characteristics of the overexpressed phytase in yeast[1]

Optimum pH[2]

| pH | 1.0 | 2.0 | 2.5 | 3.0 | 4.0 | 5.0 | 5.5 | 6.0 | 8.0 |
|---|---|---|---|---|---|---|---|---|---|
| Relative Activity (%) | .5$^e$ ± .2 | 59.7$^c$ ± 3 | 64.8$^c$ ± 6 | 48.1$^d$ ± 4 | 81.0$^b$ ± 5 | 100.0$^a$ ± 1 | 95.0$^a$ ± 6 | 66.3$^c$ ± 1 | .8$^e$ ± .4 |

Optimum Temperature[3]

| ° C. | 25 | 37 | 45 | 50 | 55 | 60 | 75 | 80 |
|---|---|---|---|---|---|---|---|---|
| Relative activity (%) | 24.2$^e$ ± .8 | 44.6$^d$ ± 3 | 63.9$^c$ ± 8 | 83.6$^b$ ± 2 | 89.8$^b$ ± 4 | 100.0$^a$ ± 4 | .6$^f$ ± .1 | .9$^f$ ± .2 |

[1]Data are means of relative activity ± standard deviation (n = 4). Means in a row with different superscript letters differ (P < 0.05). The general linear model of the statistical analysis system (1988) was used to analyze the main treatment effects as randomized complete designs and Bonferroni t-test was used for multiple treatment mean comparison. Significance level was set as P < 0.05.
[2]The activity was assayed at 37° C. (see context for phytase unit definition). Different buffers were used: 0.2 mM glycine-HCl buffer for pH 1.0 to 3.5; 0.2 mM sodium citrate buffer for pH 4.0 to 6.5; and 0.2 mM Tris-HCl buffer for pH over 7.
[3]Optimum temperature was determined at pH 5.5 (0.2 mM sodium citrate buffer).

TABLE 5

Comparison of the thermostability of overexpressed phytase in yeast and Gist-Brocades phytase produced by *A. niger*[1,2]

| Relative activity, % | 37° C. | 80° C. |
|---|---|---|
| Yeast phytase | 100$^a$ ± 1 | 63$^b$ ± 1 |
| *A. niger* phytase | 100$^x$ ± 3 | 52$^y$ ± 2 |
| P[3] | < | .03 |

[1] Data are means of relative activity ± standard deviation (n = 3). Means in a row with the different superscript letters differ (P < 0.05). The general linear model of the statistical analysis system (1988) was used to analyze the main treatment effects as randomized complete designs and Bonferroni t-test was used for multiple treatment mean comparison. Significance level was set as P < 0.05.
[2] The enzyme was heated for 15 minutes at different temperatures before reacting at 37° C. and pH 5.5.
[3] Significance (P values) of t-test between the activity of the two phytases at each temperature setting.

Although it is unclear how such improvement in thermostability is related to different post-translational modifications (folding, cleavage, glycosylation, etc.), (Li, X. L. et al., "Expression of *Aureobasidium Pullulans* XynA in, and Secretion of the Xylanase From, *Saccharomyces Cerevisiaea*," *Appl. Environ. Microbiol.,* 62:209–13 (1996), which is hereby incorporated by reference), it is certainly advantageous to have more thermostable phytase enzyme that can hopefully be resistant to the heat during feed pelleting, which is a problem with the current Gist-Brocades phytase.

Example 6

In Vitro Hydrolysis of Phytate-P from Corn, Soy, and Wheat Middlings by the Expressed Yeast Phytase The expressed yeast phytase released phytate-P from corn and soybean meal as effectively as the Gist-Brocades phytase based on per unit activity (See Table 6). As expected, the hydrolysis of phytate-P was a function of time and activity dosage. The expressed yeast phytase was also effective in releasing phytate-P from wheat middling, indicating its great potential in bread fermentation. Because the wheat middling used in this study contained much higher intrinsic phytase activity than commonly used wheat flour, much greater effect of the expressed yeast phytase on improving flour phytate-P hydrolysis and in trace element releasing would be expected, when it is used in a bakery (Hall, M. N. et al., "The Early Days of Yeast Genetics," Cold Spring Harbor Laboratory Press (1993), which is hereby incorporated by reference).

overexpressed phytase in yeast was approximately 110 kDa, had two pH optima: 2.0 to 2.5 and 5.5 to 6.0, and the optimum temperature was at 60° C.

Example 7

Methods and Materials for Expression of phyA in *Pichia*

Host and vector. An EasySelect™ *Pichia* Expression Kit was purchased from Invitrogen (San Diego, Calif.). The kit provides hosts and vectors to express the gene either intracellularly or extracellularly, in strains of either Mut$^+$ or Mut$^s$ (Methanol utilization normal or slow). X33 was used as a Mut$^+$ strain and KM71 as a Mut$^s$ strain. Two vectors were used, pPICZ B (3.3 kb) and pPICZαA (3.6 kb), both use AOX1 as the promoter.

Construction of the Expressing Vectors. To compare the effect of different signal peptides on the expression of PhyA in *Pichia* system, two constructs were prepared. First, a 1.4 kb EcoRI-KpnI fragment, containing the PhyA sequence encoding the mature phytase protein, was ligated into pPICZαA. In this plasmid (pPICZα-phyA), PhyA was led

TABLE 6

Free phosphorus released from corn, soybean meal (SBM), and wheat middlings by overexpressed yeast phytase and fungus *A. niger* phytase in vitro[1]

| Yeast phytase (PU/kg) | | 0 | 100 | 250 | 500 | 1000 | 250 (fungus phytase) |
|---|---|---|---|---|---|---|---|
| | | | | Free phosphorus (mg/g) | | | |
| Corn: | 1 hour | .23$^d$ ± .03 | .64$^c$ ± .08 | 1.14$^b$ ± .18 | 1.46$^a$ ± .04 | 1.54$^a$ ± .04 | 1.16$^b$ ± .15 |
| | 4 hour | .36$^c$ ± .02 | 1.26$^b$ ± .04 | 1.60$^a$ ± .03 | 1.66$^a$ ± .06 | 1.72$^a$ ± .04 | 1.68$^a$ ± .04 |
| SBM: | 1 hour | .68$^d$ ± .01 | 1.18$^{cd}$ ± .02 | 1.62$^c$ ± .18 | 2.48$^b$ ± .32 | 3.13$^a$ ± .19 | 1.68$^c$ ± .2 |
| | 4 hour | .73$^d$ | 1.67$^c$ | 2.69$^b$ | 3.41$^a$ | 3.71$^a$ | 2.78$^b$ |
| Wheat | 1 hour | 3.56 ± .39 | | 4.11 ± .64 | 4.67$^2$ ± .05 | | |
| Middlings: | 4 hour | 5.63 ± .5 | | 6.02 ± .48 | 6.38$^2$ ± .07 | | |

[1]Each sample of 5 g was stirred in 20 ml of 0.2 mM sodium citrate buffer at 37° C. for 1 or 4 hours. The supernatant was obtained by spinning for 15 minutes at 8000 g. After going through Whatman 541 filter paper, the sample was subjected to free P assay by the method of Chen, P. S. et al., "Microdetermination of P," Anal.Chem., 28: 1756–58 (1956), which is hereby incorporated by reference. Data in the table are means of relative activity ± standard deviation (n = 4). The General Linear Model of the Statistical Analysis System (1988) was used to analyze the main treatment effects as randomized complete designs and Bonferroni t-test was used for multipletreatment mean comparison. Significance level was set as P < 0.05. A significant difference existed between 1 and 4 hour for every feed at each dose of enzyme as analyzed by t-test. Means in a row with different superscript letters differ (P < 0.05).
[2]n = 2

The overexpression of *Aspergillus niger* phytase (phyA) in *Escherichia coli, Streptomyces lividans,* and *Saccharomyces cerevisiae* were compared to develop an efficient and simple system to produce phytase economically. A 55 kDa soluble intracellular protein, representing 9.6% of the total soluble protein, was expressed in *E. coli* by using pET25b (+) system. A 57 kDa extracellular protein, representing 20.3% of the total protein in the medium, was expressed in *S. lividans* by using a shuttle plasmid containing the pLT1 promoter and SpeII leading peptide of endoglucanase E2. No increase in phytase activity was shown in either expression system, presumably due to the lack of glycosylation and other necessary post-translational modification. In contrast, high extracellular phytase activity was produced in *S. cerevisiae* transformed with phyA gene. Three different signal peptides and three different types of medium were compared to identify the best expression vector and condition. Use of the signal peptide Sphy from phyA gene and YEPD medium produced the highest extracellular phytase activity. The by an alpha-factor, a very general-used signal peptide from *Saccharomyces cerevisiae*. Second, a 1.4 kb KpnI-XbaI fragment of pYPP1 was ligated into the vector (the coding region of phyA was led by its own signal peptide that was very effective in secreting the expressed phytase in *Saccharomyces cerevisiae*.)

Transformation and expression. The confirmed constructs were linearized by PmeI and transformed into GS115 and KM71, by EasyComp™ provided by the kit. Neocin™ was used to select the positive colonies. After a single colony was inoculated into 10 ml of MGY medium and grown to OD$_{600}$ of 2–6 at 30° C., the cells were collected by centrifugation and resuspended into 10 ml of MMY medium (containing 0.5% of methanol). The samples were collected every 12 or 24 h after induction. The cells were separated from the supernatant and lysed with glass beads in breaking buffer. Phytase activity in the supernatant and cells was assayed as described previously. SDS-PAGE and Western blot were conducted to determine the size and relative amount of the expressed protein.

Example 8

PhyA Phytase Activity in *Pichia*

Figure 11:
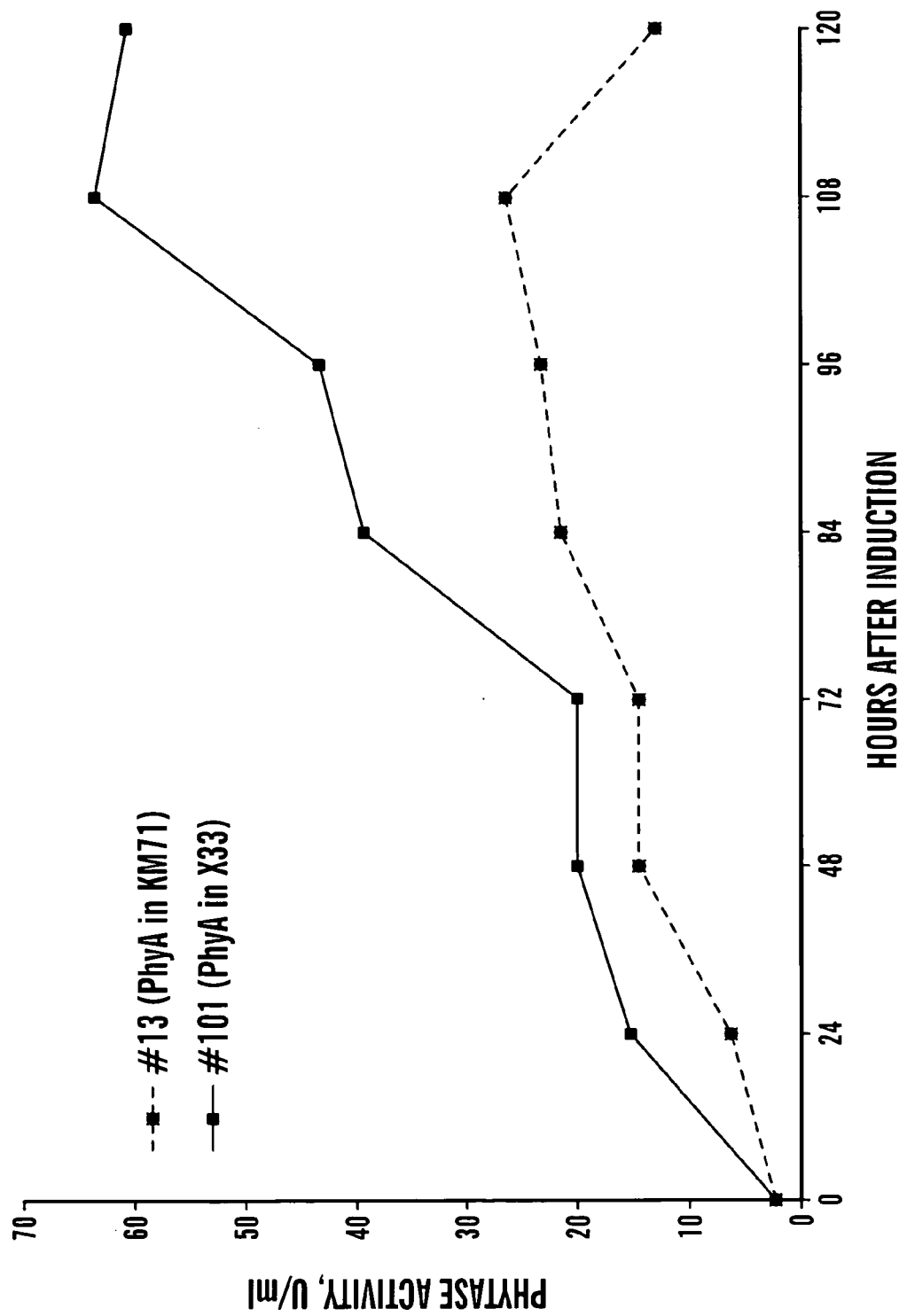
FIG. 11 is a time course of the extracellular phyA phytase activity produced by *Pichia pastoris* transformants of Mut$^s$ (KM71) and Mut+ (X33) after induction.

The expression construct using alpha-factor as the signal peptide for phyA was transformed into two *Pichia* strains. KM71 is a methanol utilization slow strain, while X33 is a *Pichia* wild-type utilizing methanol efficiently. The screening and incubation were conducted in 10 ml shake flasks under 29–30° C. For the transformants of KM71, 19 out of 20 picked colonies had extracellular phytase activity greater than 6 units/ml of culture supernatant after induction for 24 hours. Colony No. 13 showed the highest activity of 26 units/ml after incubated for 108 hours. For the transformants of X33, all colonies (20/20) had more than 10 units/ml after induced for 24 hours. One of the colonies (#101) produced phytase activity of 65 units/ml of supernatant. A time course study of the phytase expression in KM71 and X33 was summarized in FIG. 11. Despite the difference of these two strains in utilizing methanol and, therefore, the ability in expressing phytase, it was found that alpha-factor was correctly processed by yeast cells. Besides, almost all of the expressed protein was secreted into the medium since not more than 5% of the total activity expressed was found intracellularly.

Effects of inorganic phosphorus and pH of media on the phytase expression were studied in the media (BMGY and BMMY) using a phyA recombinant of X33 (#101). The medium containing 50 mM phosphate produced the highest phytase activity, 66 units/ml at 168 hours after induction. By including 50 mM phosphate in the media, the effect of different pH of this buffer (3, 4, 5, 6, 7, and 8) on expression was also studied. When the pH was 6, this X33 transformant produced 75 units phytase/ml supernatant. Based on the protein concentration and SDS-PAGE analysis, the expression phytase protein yield was estimated to be between 3 to 4 mg/ml.

Example 9

Properties of the PhyA Phytase Expressed in *Pichia*

Figure 12:
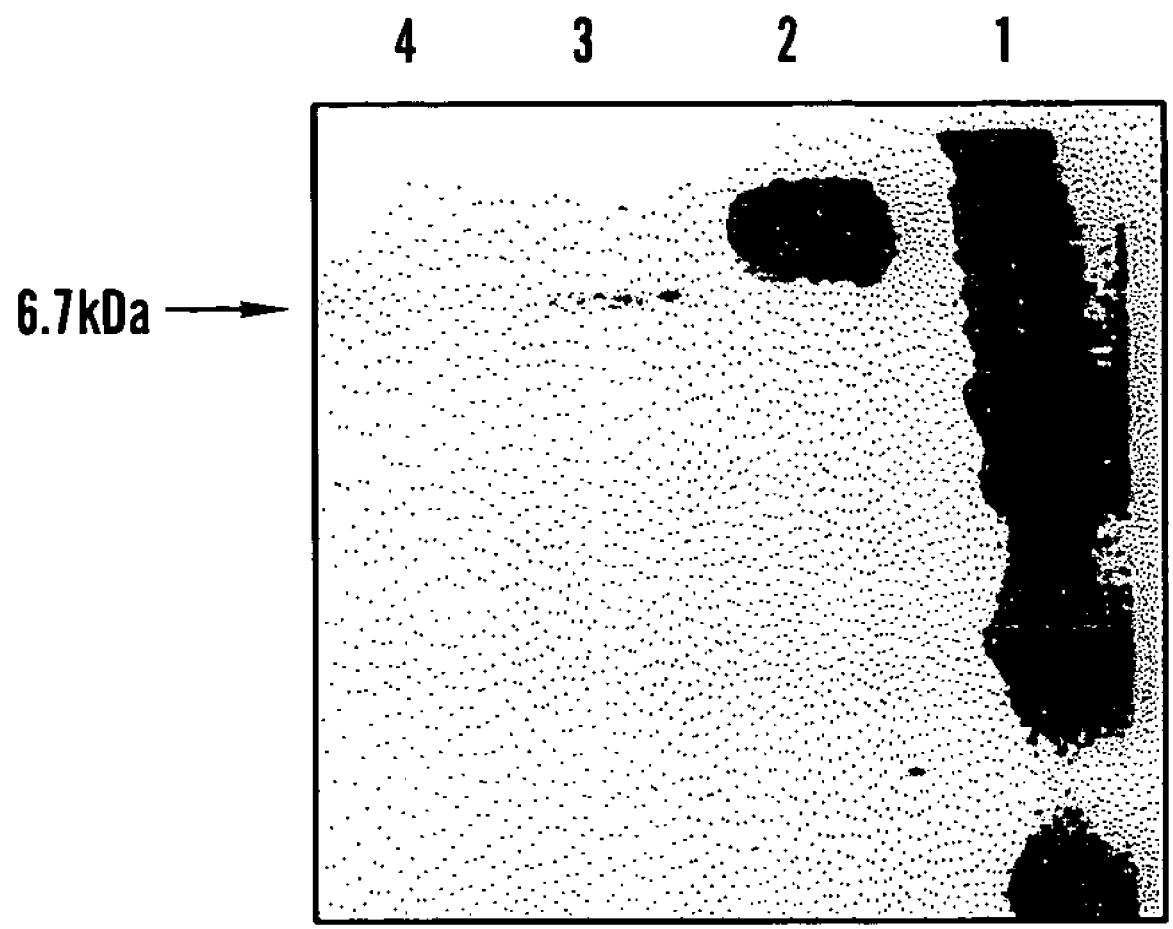
FIG. 12 depicts an SDS-PAGE analysis of the overexpressed phytase in *Pichia*, with construct of pPICZαA-PhyA in KM71 (MUT$^s$). Lane 1: protein ladder. Lane 2: 40 μl of the supernatant of AK1 (a colony showed 21,700 mU/ml of extracellular phytase), collected 108 hours after induction. Lane 3: 40 μl of the supernatant of a control strain overexpressing human serum albumin (HAS, 6.7 kDa) at a level of 1 g/L. Lane 4: 40 μl of the supernatant of the KM71 control.
Figure 13:
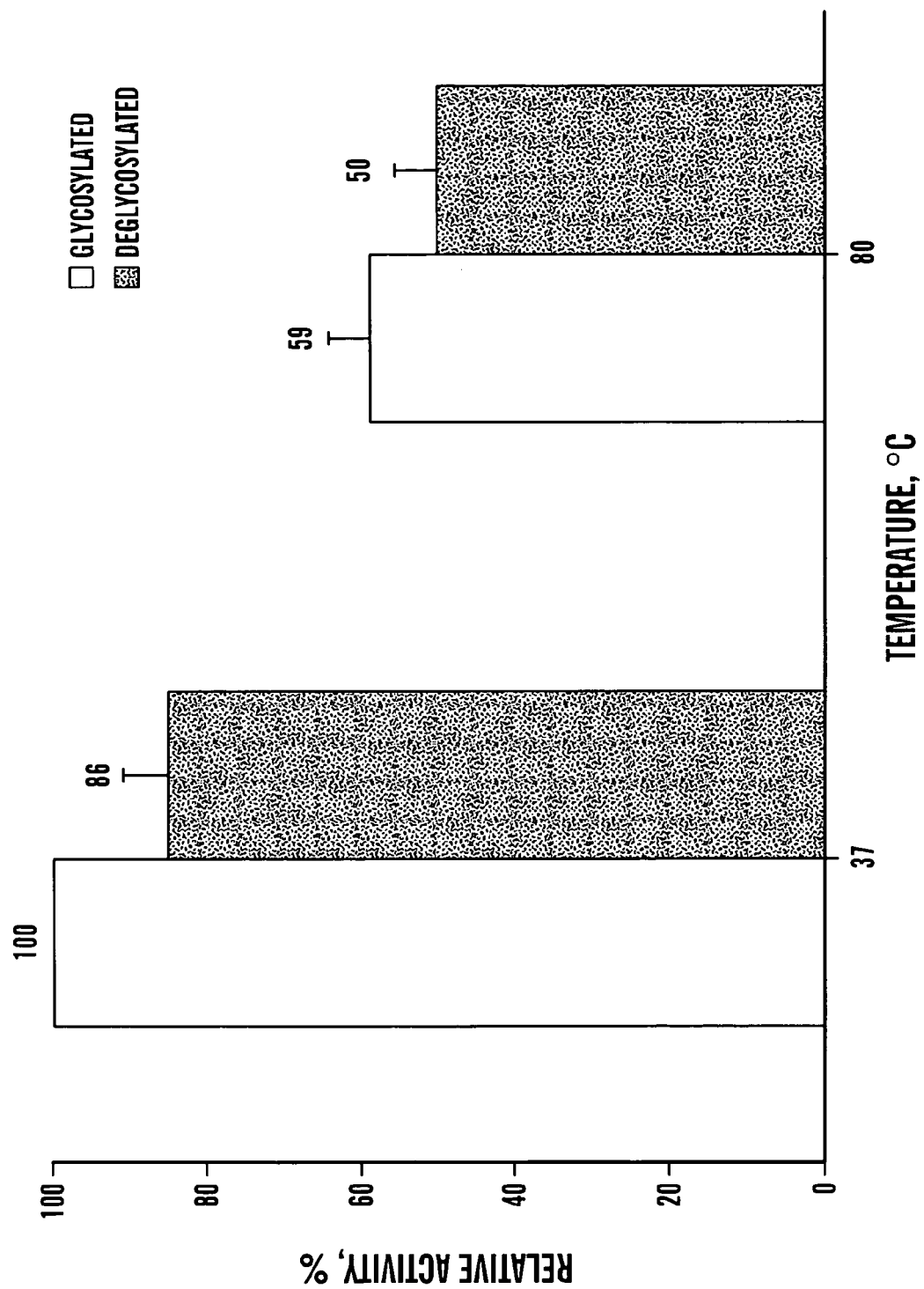
FIG. 13 depicts effects of deglycosylation by Endo H on the thermostability of the expressed phytase in *Pichia*. Phytase activity was measured after the enzymes were heated for 15 minutes under 37 or 80° C. in 0.2 M citrate buffer, pH 5.5.

Molecular size and deglycosylation of the expressed phytase. After the supernatant of the medium inoculated with the phyA transformant was subjected to SDS-PAGE, a strong band around 95 kDa was seen (FIG. 12). This was almost the only viewed protein in the supernatant. The expressed phytase reacted efficiently with the rabbit polyclonal antibody raised against purified native *A. niger* phytase. This indicated that the immunoreactivity of the expressed phytase was essentially the same as that of the native phytase from *A. niger*. The size was decreased to 50 kDa by deglycosylation using Endo H. The phyA antibody also reacted with the deglycosylated phytase. In addition, deglycosylation, conducted under native conditions, reduced the phytase activity about 15%, indicating that glycosylation was important for the activity of the phytases. Moreover, glycosylation affected the thermostability of the enzymes (FIG. 13).

Figure 14:
FIG. 14 is a scan image of Northern analysis of the expressed phyA mRNA by the transformed *Pichia pastoris* strains (KM71 and X33). A 1.3 kb phyA probe was used for blotting. Lanes 1 and 2: the transformant of KM71 before and after induction; Lanes 3 and 4: the transformant of X33 after and before induction.

Northern analysis. As showed in FIG. 14, a 1.3 kb phyA DNA probe hybridized with the mRNA of the induced transformants from both KM71 (#13) and X33 (#101). Response was also seen from the transformants prior to induction. Probably, the expression of phyA in this system was not controlled strictly at the level of transcription.

Figure 15:
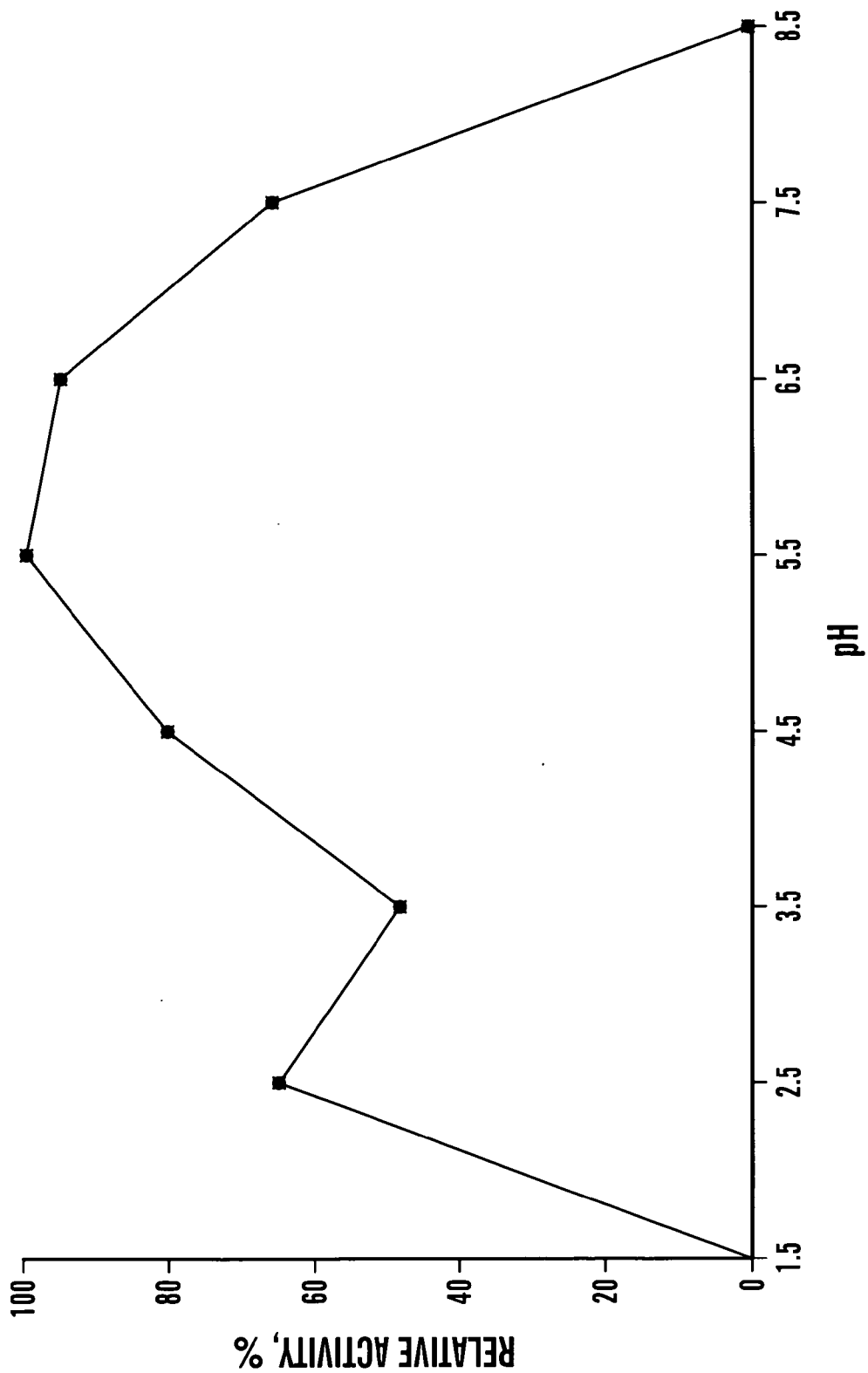
FIG. 15 shows the optimum pH of the expressed extracellular phytase by *Pichia* (X33). Buffers of 0.2 M glycine-HCl for pH 1.5, 2.5, 3.5; 0.2 M sodium citrate for pH 4.5, 5.5, 6.5, and 0.2 M Tris-HCl for pH 7.5 and 8.5 were used.
Figure 16:
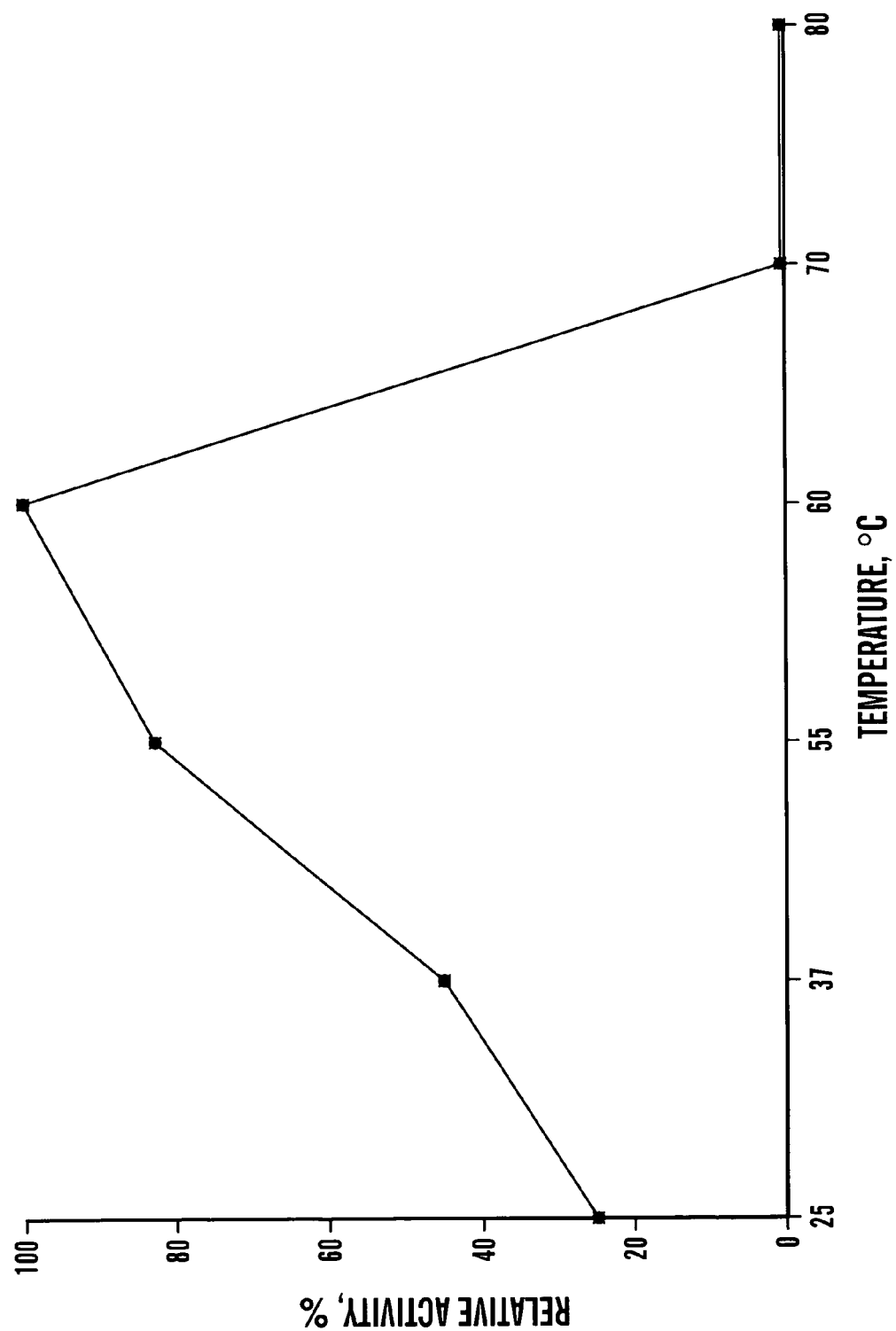
FIG. 16 shows the optimum temperature of the expressed extracellular phytase by *Pichia* (X33). The assays were conducted in 0.2 M citrate buffer, pH 5.5.
Figure 17:
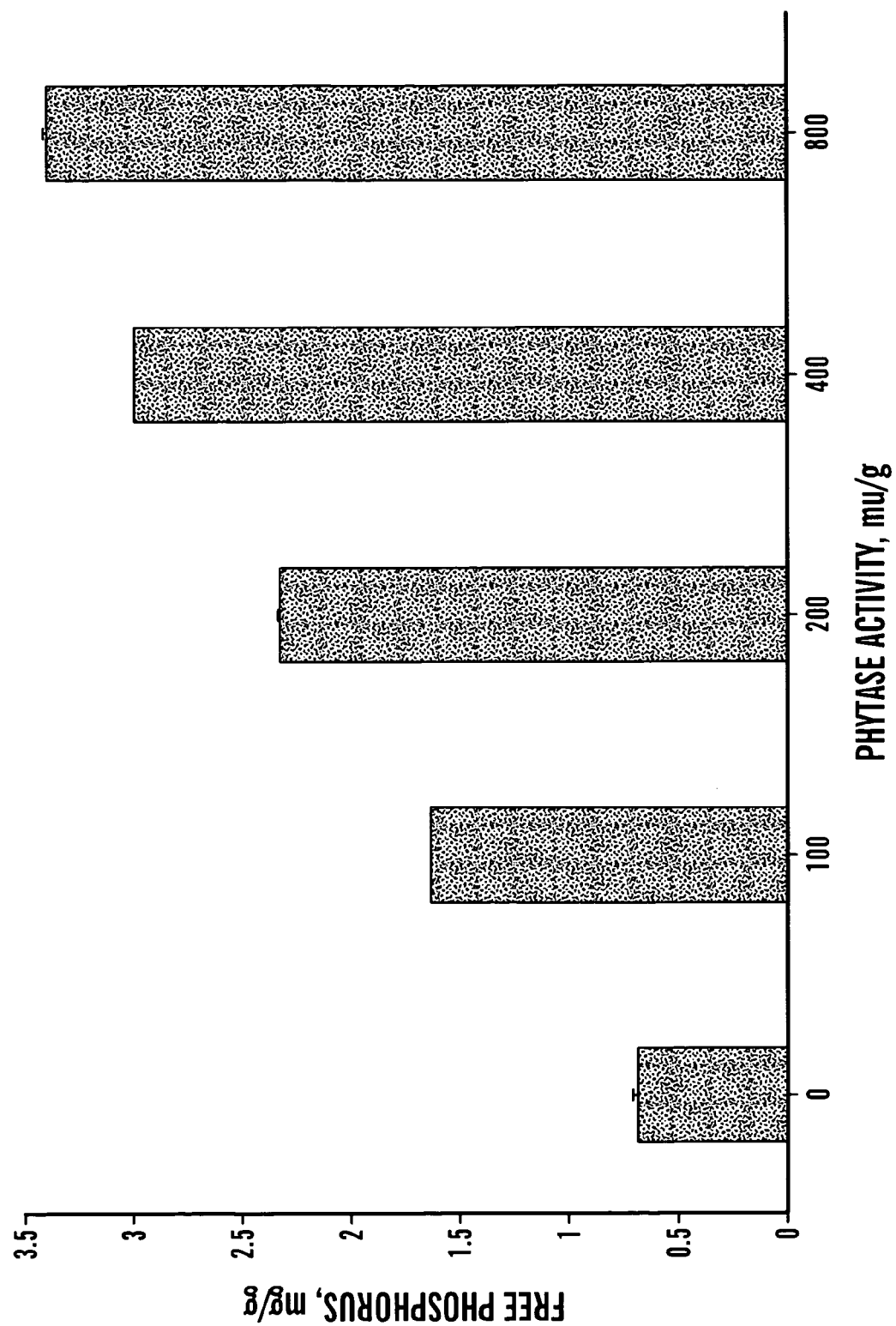
FIG. 17 depicts the release of free phosphorus from soybean by the expressed phytase in *Pichia* (X33). Five grams of soybean were suspended in 25 ml of 0.2 M citrate, pH 5.5, with different amounts of the enzyme. The incubation was conducted for 4 hours under 37° C. and the free phosphorus released in the supernatant was determined.

Optimal pH and temperature and phytate-phosphorus hydrolysis. Similar to *A. niger* phytase, the expressed phytase had two optimum pH, 2.5 and 5.5 (FIG. 15). The optimum temperature of the expressed phytase was 60° C. (FIG. 16). When the expressed phytase was incubated with soy samples at 100, 200, 400, 800 mU/g of sample at 37° C., phosphorus was released in a linear fashion with the phytase dose (FIG. 17).

Example 10

Methods and Materials for Overexpression of *E. coli* appA Gene in *Saccharomyces cerevisiae*

Gene and Protein. This gene, originally defined as *E. coli* periplasmic phosphoanhydride phosphohydrolase (appA) gene, contains 1,298 nucleotides (GeneBank accession number: M58708). The gene was first found to code for an acid phosphatase protein of optimal pH of 2.5 (EcAP) in *E. coli*. The acid phosphatase is a monomer with a molecular mass of 44,644 daltons. Mature EcAP contains 410 amino acids (Dassa, J. et al., "The Complete Nucleotide Sequence of the *Escherichia coli* Gene appA Reveals Significant Homology Between pH 2.5 Acid Phosphatase and Glucose-1-Phosphatase," *J. Bacteriology*, 172:5497–5500 (1990), which is hereby incorporated by reference). Ostanin, K. et al. ("Overexpression, Site-Directed Mutagenesis, and Mechanism of *Escherichia coli* Acid Phosphatase," *J. Biol. Chem.*, 267: 22830–36 (1992), which is hereby incorporated by reference), overexpressed appA in *E. coli* BL21 using a pT7 vector and increased its acid phosphatase activity by approximately 400-fold (440 mU/mg protein).

The gene and a host *E. coli* strain CU 1869 (No. 47092) were purchased from ATCC. The gene, an insert of 1.3 kb, was transformed into *E. coli* strain BL21 (no. 87441) using an expression vector pAPPA1 (Ostanin, K. et al., "Overexpression, Site-Directed Mutagenesis, and Mechanism of *Escherichia coli* Acid Phosphatase," *J. Biol. Chem.*, 267: 22830–36 (1992), which is hereby incorporated by reference).

Host and Vector. The vector for overexpressing appA gene in *Saccharomyces cerevisiae* was pYES2 and the host was INVScI (Invitrogen, San Diego, Calif.).

Construction of the Expression Vector. Initially, a 1.3 kb XbaI fragment was isolated from pAPPA1. This fragment contained the appA gene with its own signal peptide. After being ligated into the XbaI site of pYES2, the construct (PYES2-appA) was transformed into *Saccharomyces cerevisiae*. But, no phytase activity was increased in either extra- or intra-cellular parts compared to the controls. pAPPA1 and pYPP1 (PhyA and its signal peptide in pYES2) were cotransformed into the yeast strain. Again, no increase in phytase activity due to pAPPA1 was detected in the media or the yeast cells.

Two primers were synthesized to construct the signal peptide of PhyA gene with the coding region of appA gene. One was 80 bp long containing the PhyA signal peptide and a KpnI site at 5' end: GGG GTA CCA TGG GCG TCT CTG CTG TTC TAC TTC CTT TGT ATC TCC TGT CTG GAG TCA CCT CCG GAC AGA GTG AGC CGG AG (SEQ ID NO:9). The other primer was 24 bp long, with an EcoRI site at its 3' end: GGG AAT TCA TTA CAA ACT GCA GGC (SEQ ID NO:10). The PCR was run for 25 cycles, with 1 min denaturing at 95° C., 1 min annealing at 58° C., and 1 min chain extending at 72° C. A 1.3 kb fragment was amplified, digested, and ligated into pYES2. After the insert was confirmed by restriction mapping, the construct (pYES2-SphyA-appA) was transformed into INVScI by lithium acetate method.

Expression. The selected transformants were inoculated into YEPD medium. The expression was induced by adding galactose into the culture after $OD_{600}$ reached 2, as described previously. The cells were harvested 15 or 20 h after induction.

Activity Assay. Acid phosphatase activity was assayed at 37° C. in 25 mM glycine-HCl buffer (pH 2.5), using p-nitrophenyl phosphate as the substrate (stock 250 mM). Reaction buffer of 1.7 ml was added into 0.1 ml samples. After they were incubated for 5 min in a 37° C. waterbath, 0.2 ml of prewarmed substrate was added and mixed. The reaction solution was transferred into a prewarmed cuvette and incubated for 2 min in a 37° C. spectrophotometric compartment. The released p-nitrophenol was read continuously for 5 min at 405 nm for enzyme activity calculation.

In vitro study. Soybean meal (5.0 g) was suspended into 20 ml of 20 mM citrate buffer, pH 5.5, mixed with 200 mU of phytase, incubated at 37° C. for 4 h with continuous shaking. After chilling on ice for 10 min, the slurry was transferred into a centrifuge tube and spun for 15 min at 15,000×g. The supernatant was used to determine free phosphorus.

Example 11

Quantitation of Phytase Activity from Overexpression of *E. coli* appA Gene in *Saccharomyces cerevisiae*

The intracellular acid phosphatase activity in the appA overexpressed *E. coli* (pAPPA1) was 440 mU/mg protein. Unprecedently, an intracellular phytase activity greater than 4900 mU/mg protein was found in the transformed strain. But, there was only minimal phytase activity in the control (BL21). Thus, this acid phosphatase gene also codes for a phytase. The appA gene sequence was aligned with that of PhyA and found that these two genes shared 23% of identity.

Transforming INVScI with the construct of pYES2-Sphy-appA (led by the signal peptide of PhyA) produced extracellular phytase activity in the supernatant that was 2,000-fold greater than those of the wild type or of the transformant containing appA gene plus its own signal peptide (See Table 7).

TABLE 7

Extracellular phytase activity in transformants of appA gene with different signal peptides

| Construct | Signal | Activity (mU/ml) | Activity (mU/mg protein) |
|---|---|---|---|
| PYES-appA | appA | Undetectable | Undetectable |
| pYES2-SphyA-appA | PhyA | 1,158 | 445 |

The effects of medium (YEPD) inorganic phosphorus, phytate, pH, and temperature on the expression of phytase activity by pYES2-Sphy-A-appA are presented in Table 8. The highest phytase activity was 2,286 mU/ml (633 mU/mg protein) at the optimal condition.

TABLE 8

Effect of different conditions in the YEPD medium on phytase activity expression of pYES2-SphyA-appA in yeast.

| Medium Conditions | Activity (mU/ml) |
|---|---|
| Phosphorus, mg/100 ml | |
| 0 | 1402 |
| 1 | 714 |
| 5 | 722 |
| 10 | 456 |
| Sodium phytate, g/100 ml | |
| 0 | 870 |
| 0.1 | 1019 |
| 1.0 | 1748 |
| Ph | |
| 5.0 | 892 |
| 7.0 | 996 |
| 8.0 | 2286 |
| Temperature, ° C. | |
| 25 | 312 |
| 30 | 1036 |
| 37 | 996 |

The thermostability of the overexpressed extracellular phytase activity produced by the yeast transformant was greater than that of the intracellular phytase produced by *E. coli* transformed with pAPPA1 (See Table 9). Heating the extracellular phytase for 15 min at 80° C. resulted in 30% of loss of its phytase activity, while almost all the phytase activity from *E. coli* was lost under the same condition.

TABLE 9

Effect of heating different sources of phytases under 80° C. for 15 min on their activities

| Phytase | Relative activity after heating, % |
|---|---|
| appA in *E. coli* | 0.1 |
| appA in *S. cerevisiae* | 69 |
| PhyA in *S. cerevisiae* | 66 |
| BASF phytase | 50 |

Comparisons of the effect on releasing phosphorus from soybean meal by phytases (200 mU) of *E. coli*, overexpressed AppA in yeast, and BASF are presented in Table 10. The results indicate that all three sources of phytases released phytate-phosphorus effectively from soybean meal.

TABLE 10

Free phosphorus released from soybean meal by different sources of phytases

| Phytase | Phosphorus (mg/g) |
|---|---|
| appA in *E. coli* | 1.11 |
| appA in *S. cerevisiae* | 0.69 |
| BASF | 0.87 |

*E. coli* appA (acid phosphatase) gene when expressed in *Sacchacromyces cerevisiae* produces extracellular phytase activity in the media that was more than 2,000-fold greater than the control. The overexpressed phytase effectively releases phytate-phosphorus from soybean meal, and seems to be more thermostable than the presently available commercial phytase or the intracellular phytase produced in *E. coli* by the same gene (appA).

Example 12

Methods and Materials for Overexpressing the *E. coli* appA Gene Encoding an Acid Phosphatase/Phytase in *Pichia pastoris*

Gene and Protein. The appA gene and the host *E. coli* strain CU1867 (No. 47092) were obtained from ATCC. The gene, an insert of 1.3 kb, was transformed into *E. coli* strain BL21 (No. 87441) using an expression vector pAPPA1 (Ostanin, K. et al., "Overexpression, Site-Directed Mutagenesis, and Mechanism of *Escherichia coli* Acid Phosphatase," *J. Biol. Chem.*, 267:22830–36 (1992), which is hereby incorporated by reference).

Host and Vector. An EasySelect™ *Pichia* Expression Kit was obtained from Invitrogen (San Diego, Calif.). The kit provides hosts and vectors to express the gene either intracellularly or extracellularly in a wild-type strain (X-33). Two vectors were used, pPICZ B (3.3 kb) and pPICZαA (3.6 kb), both use AOX1 as the promoter.

Construction of the Expression Vector. Two primers were used to amplify the appA gene from pAPPA1 and two restriction sites EcoRI and KpnI were produced at the 5' and 3' ends, respectively.

```
                                    (SEQ ID NO:11)
Upstream primer: GGA ATT CCA GAG TGA GCC GGA (SEQ ID NO:12)
Downstream primer: GGG GTA CCT TAC AAA CTG CAC G
```

Template: pAPPA1 DNA isolated from ATCC 87441

PCR was run for 30 cycles, with 1 min denaturing at 94° C., 1 min annealing at 55° C., and 1 min chain extending at 72° C. A 1,245 base-pair fragment was amplified, digested with EcoRI and KpnI, and ligated (16° C. overnight) into pPICZ B (3.3 kb) and pPICZαA (3.6 kb). The ligation was confirmed by restriction mapping after transforming the constructs into DH5α.

Transformation of the construct into *Pichia* (X33). For each transformation, 100 μg of plasmid DNA was prepared and linearized by digesting with PmeI. After linearization, the DNA was purified and resuspended into 10 μL of sterile, deionized water. Half amount of the DNA was actually used for each transformation. Electroporation and the EasyComp chemical kit (Invitrogen) were both used to transform the DNA into X33. In the case of electroporation, an Electro Cell Manipulator (ECM 600, Gentromics, BTX Instrument Division, San Diego, Calif. 92121) and 2 mm cuvettes were used. The resistance was 186 Ohm, the charging voltage was 1.5 kilovolts, and the actual charging length was approximately 7 milliseconds. The electroporated cells were incubated on YPD agar plates containing 100 mg Zeocin/mL at 30° C. for 2–4 days for colony growth. In the case of chemical transformation, cells were grown on YPDS agar plates containing 100 mg Zeocin/mL. Compared with the electroporation, the chemical method had lower transformation efficiency.

Expression. Single colonies were inoculated into 10 ml of MGY medium (30 ml tube) and grown (16–18 h) to $OD_{600}$ of 5–6 at 28–30° C. in a shaking incubator (200 rpm). The cells were collected by centrifugation (2,000 rpm) and resuspended into 10 ml of BMMY medium (containing 0.5% of methanol) to induce the expression. The samples (200 μL) were collected every 12 or 24 h after induction. Methanol (100%) was added at 100 μL every 24 to maintain a concentration of 0.5–1% in the media.

Assays. The cells were separated from the media (supernatant) and lysed with glass beads in breaking buffer. Extracellular phytase activity in the supernatant and intracellular phytase activity in the lysed cells were assayed as described previously (0.2 M citrate buffer, pH 5.5 under 37° C. using 10 mM sodium phytate). Acid phosphatase activity was assayed at 37° C. in 25 mM glycine-HCl buffer (pH 2.5), using p-nitrophenyl phosphate as the substrate (stock 250 mM). Reaction buffer of 1.7 ml was added into 0.1 ml samples. The released p-nitrophenol was read continuously for 5 min at 405 nm for enzyme activity calculation. SDS-PAGE (12%) was conducted to determine the size and relative amount of the expressed protein. The optimal pH and temperature of the expressed phytase were determined as described in the results.

In vitro study. Soybean meal (5.0 g) was suspended into 20 ml of 20 mM citrate buffer, pH 5.5, mixed with different levels of phytase, and incubated at 37° C. for 4 h with continuous shaking. After being chilled on ice for 10 min, the slurry was transferred into a centrifuge tube and spun for 15 min at 15,000×g. The supernatant was used to determine free phosphorus.

Example 13

Colony Phytase Activity Screening for *Phicia pastoris* Overexpressing the *E coli* appA Gene Wild-type *Pichia* X33 produces minimal phytase activity intracellularly (<0.03 U/mg protein) or extracellularly (<0.05 U/mL). The X33 cells transformed with the appA gene inserted into pPICZB (without the α-factor and presumably produces intracellular phytase) did not show any increase in phytase activity (extracellular, 0.2 U/mL and intracellular, 0.05 U/mg protein).

Transforming X33 cells with the construct of pPIZαA-appA (led by the signal peptide of α-factor) produced extracellular phytase activity in the media. Initially, 72 colonies were screened. Only two colonies had activity <1 U/mL 40 hours after induction. Most of the colonies had activity ranging from 10 to 20 U/mL 40 hours after induction. All of the 70 colonies had phytase activity >80 U/mL 118 hours after induction. The highest phytase activity so far detected was 215 U/mL, 192 hours after the induction (See Table 11).

TABLE 11

Range of extracellular phytase activity in X33 colonies transformed with pPIZαA-appA 40 and 118 hours after induction.

| Number of Colonies | 40 hours after induction | 118 hours after induction |
|---|---|---|
| 2 | <1 U/mL | |
| 6 | 1 to 10 U/mL | |
| 36 | 11 to 20 U/mL | |
| 28 | >20 U/mL | |
| 70 | | >80 U/mL |

Phytase and acid phosphatase activities in the transformant expressing 215U phytase activity/mL were compared with those of the wild-type of X33 (192 hours after induction) (See Table 12). Almost all of the expressed phytase protein was secreted from the cells, indicating that α-factor was a very effective signal peptide for phytase secretion.

TABLE 12

Phytase and acid phosphatase activities in the pPIZαA-appA transformant and the wild-type of X33 192 hours after induction.

|  | Wild-type X33 | | pPIZαA-appA transformant | |
| --- | --- | --- | --- | --- |
|  | Extra-cellular U/mL | Intra-cellular U/mg protein | Extra-cellular U/mL | Intra-cellular U/mg protein |
| Phytase | 0.05 | 0.03 | 215 | 0.5 |
| Acid phosphatase | 0.01 | 0.002 | 5.88 | 0.9 |

Transformants of *E. coli* with the same acid phosphatase appA gene had intracellular phytase activity of 5 U/mg protein (Ostanin et al., "Overexpression, Site-Directed Mutagenesis, and Mechanism of *Escherichia coli* Acid Phosphatase," *J. Biol. Chem.*, 267:22830–36 (1992), which is hereby incorporated by reference). Transforming PhyA gene in *A. niger* produced an extracellular activity of 7.6 U/ml (Hartingsveldt et al., "Cloning, Characterization and Overexpression of the Phytase-Encoding Gene (phyA) of *Aspergillus Niger*," *Gene* 127:87–94 (1993), which is hereby incorporated by reference). Compared with these results, the phytase expression system in *Pichia* is a very efficient expression system.

Example 14

Time-Course of Phytase Expression

Figure 18:
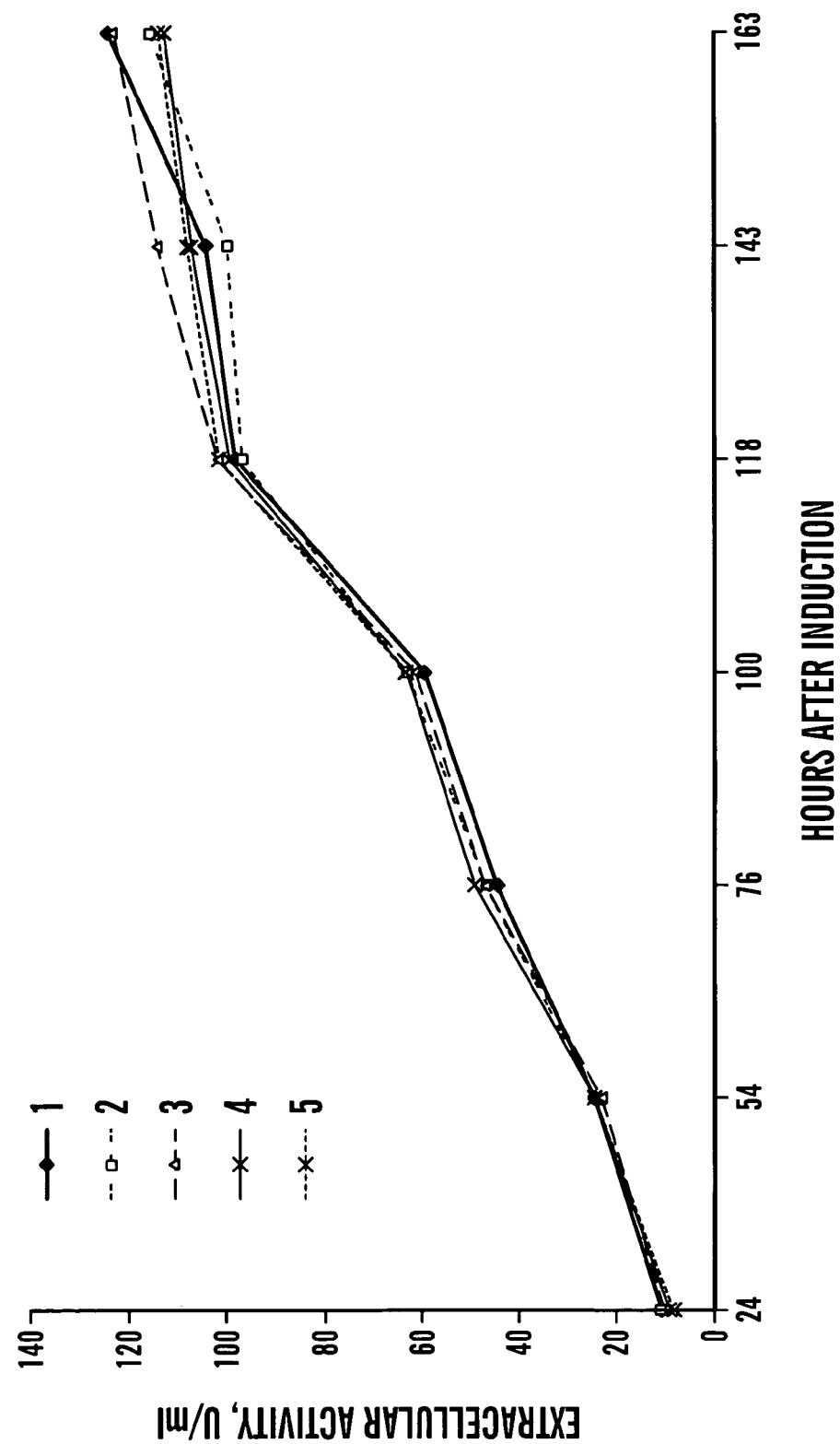
FIG. 18 shows a time course of the expression of the extracellular phytase activity from five transformants of *Pichia pastoris* containing the *E. coli* appA gene.

There was a linear increase in extracellular phytase activity in the media almost in all of the selected colonies up to 192 hours after induction. FIG. 18 summarized the activity changes of five selected colonies from 24 to 163 hours after induction.

Example 15

Effects of Medium pH on the Expression of Phytase (Colony #23, Activity 136 U/mL at 186 h)

Figure 19:
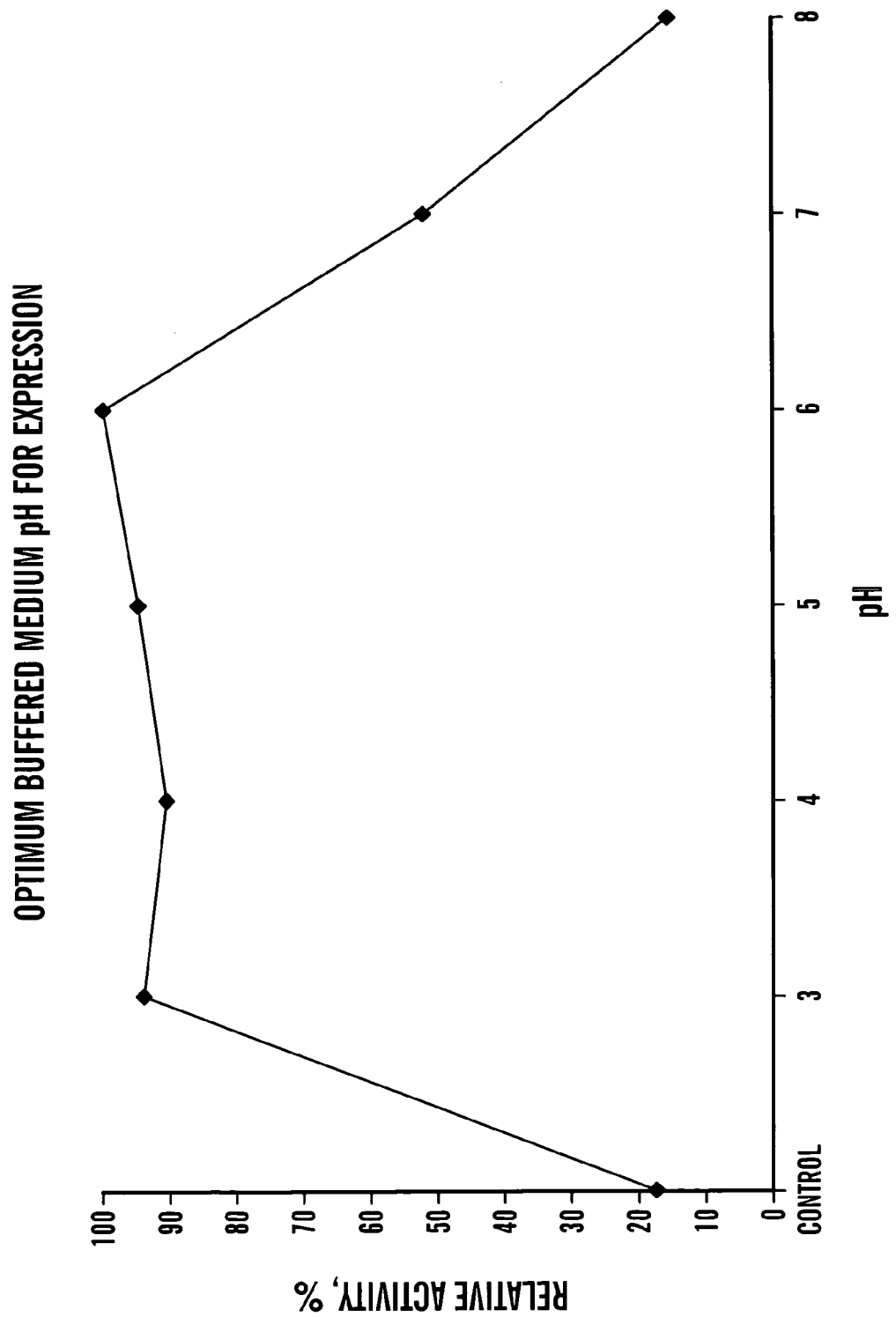
FIG. 19 graphically shows the relationship between medium pH and the expression of phytase activity by *Pichia pastoris*.

Using 0.1 M phosphate buffered media, the effects of different pH on the production of extracellular phytase in the transformants were studied against a control medium without buffer (pH 7.0). The medium buffered to pH 6 produced the highest phytase activity (See FIG. 19).

Example 16

Size of the Expressed Extracellular Phytase

Figure 20:
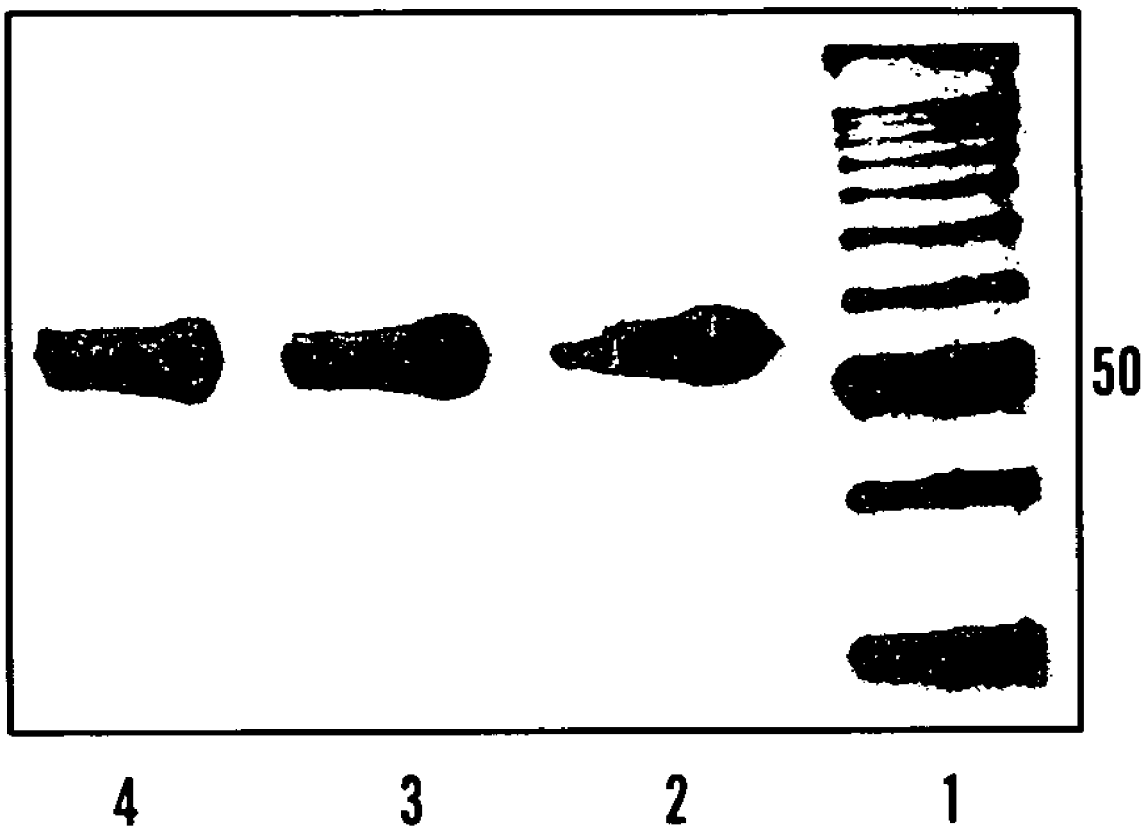
FIG. 20 is an SDS-PAGE analysis of the *E. coli* phytase overexpressed in *Pichia pastoris*. Lane 1: Protein ladder; Lanes 2 to 4: Supernatants collected from the cultures of positive colonies 23, 22, and 11, respectively, at 118 hours after induction.

Using SDS-PAGE (12% gel) analysis, a clear band was noticed in the medium supernatant of culture inoculated with three different colonies (See FIG. 20). The size was around 55 kDa, probably partially glycosylated. Because the expressed protein represented almost the only visible band in the supernatant, it would be convenient to collect the enzyme product without the need for a tedious purification.

Example 17

Optimum pH and Temperature of the Expressed Extracellular Phytase (Colony #23)

Figure 21:
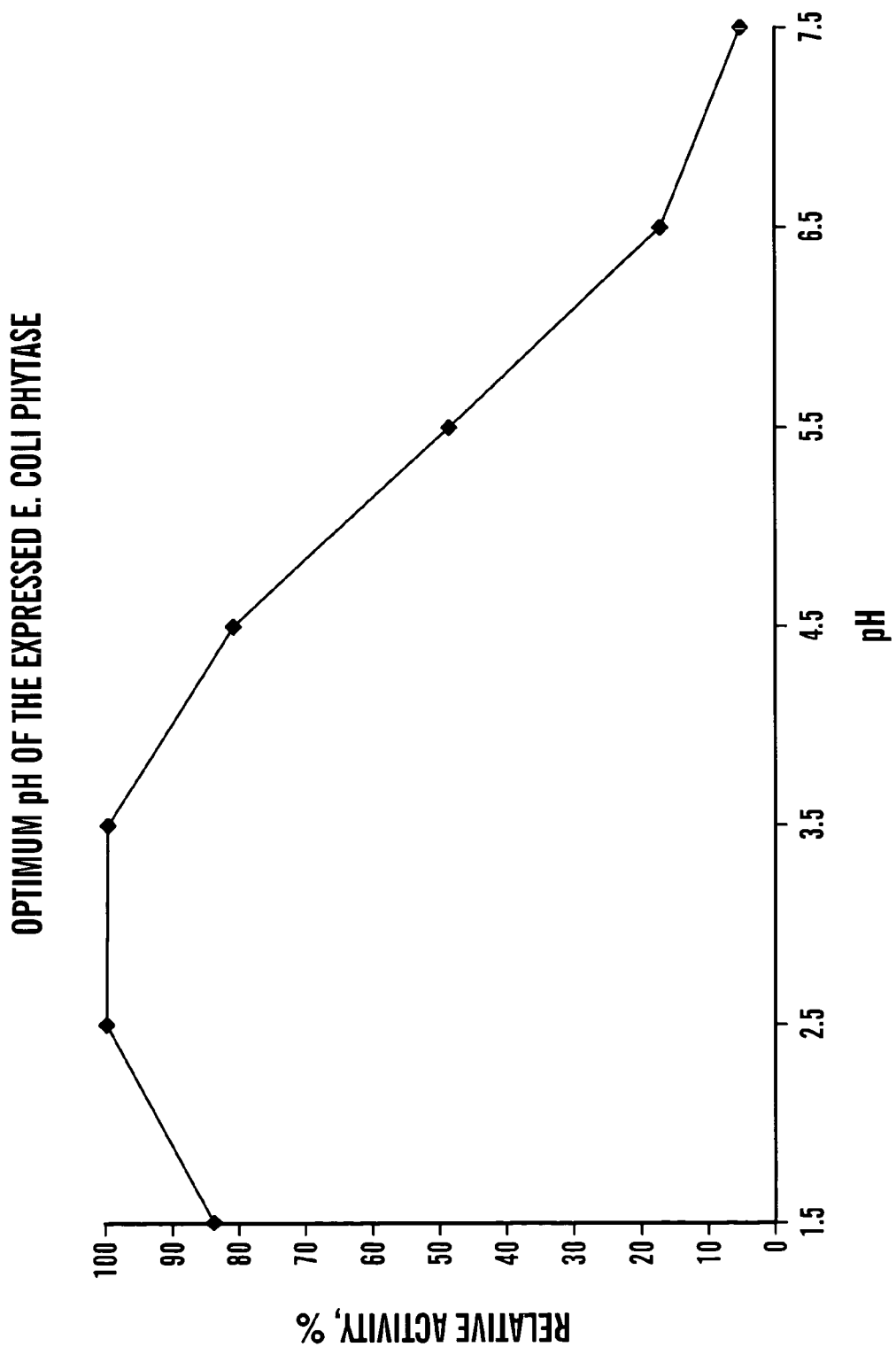
FIG. 21 graphically shows the optimum pH of the overexpressed *E. coli* phytase by *Pichia pastoris*.

The optimum pH of the expressed phytase was 2.5 to 3.5 (See FIG. 21). This is significantly different from that of phyA phytase either from *A. niger* (BASF) or our other expression systems. It is ideal for phytase function at the stomach pH.

Figure 22:
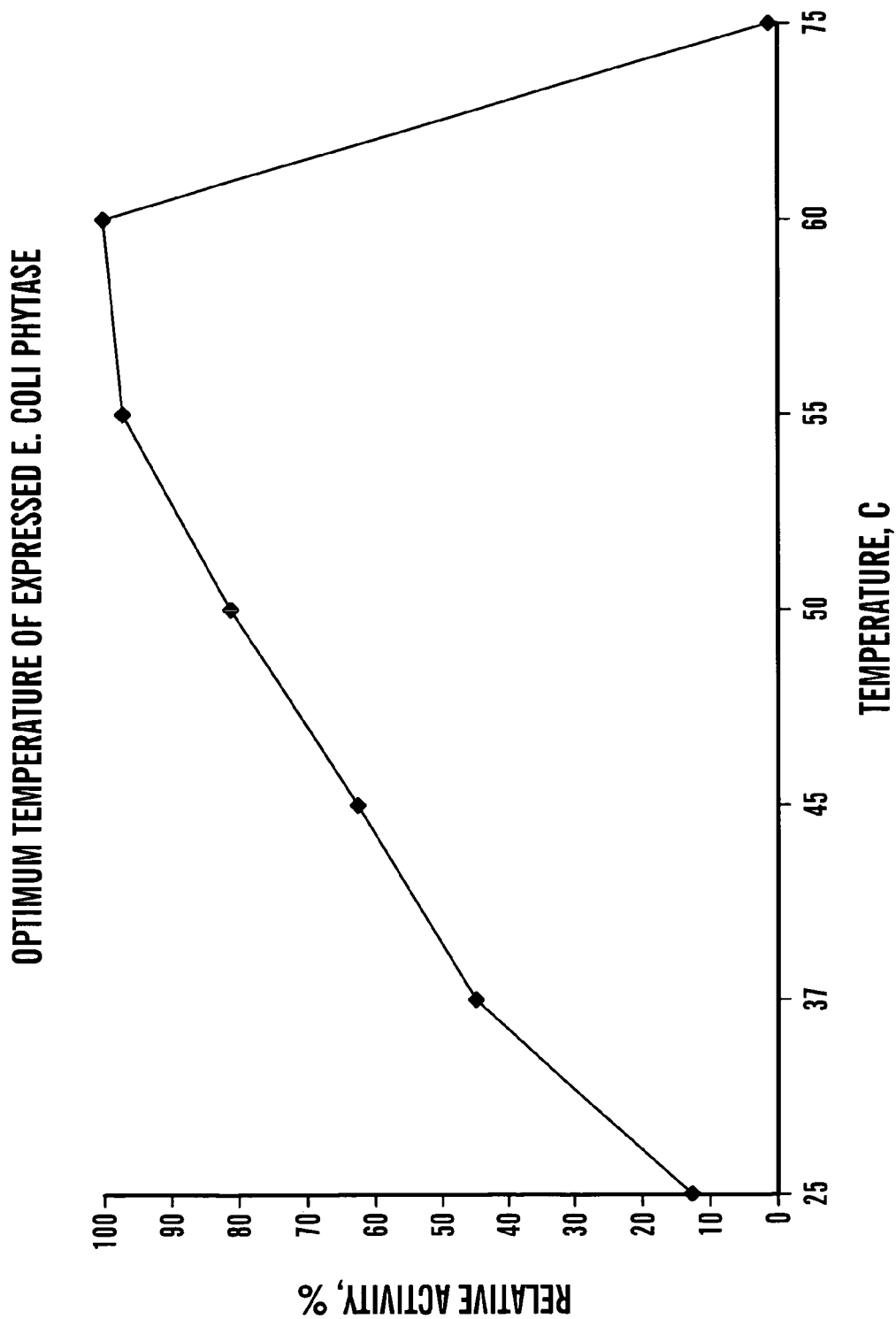
FIG. 22 graphically shows the optimum temperature of the overexpressed *E. coli* phytase by *Pichia pastoris*.

The optimum temperature of the expressed enzyme was 60° C. (See FIG. 22).

Example 18

Figure 23:
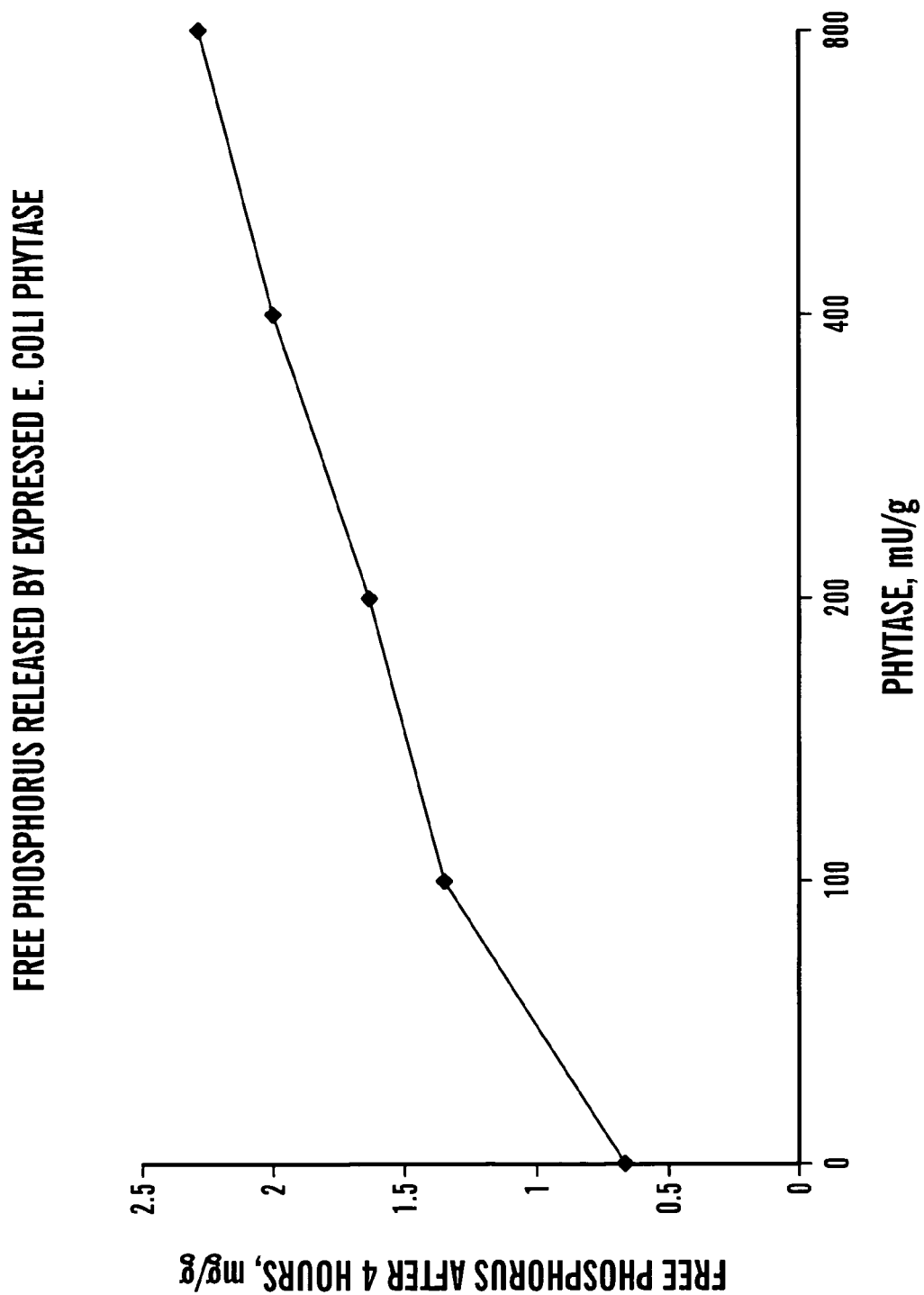
FIG. 23 shows the amount of free phosphorus released from soybean meal by the overexpressed *E. coli* phytase from *Pichia pastoris* after four hours treatment.

Effect of the Expressed Phytase on Phytate-Phosphorus Hydrolysis from Soybean Meal This overexpressed *E. coli* phytase (Colony #23) effectively hydrolyzed phytate-phosphorus from soybean meal (See FIG. 23). The release of free phosphorus in the mixture was linear from 0 to 800 mU of phytase/g of feed.

Example 19

Effects of the Expressed *E. coli* AppA Phytase by *Pichia pastoris* on Phytate Phosphorus Bioavailability to Weanling Pigs To determine the nutritional values of the expressed *E. coli* phytase by *Pichia* in swine diets, the efficacy of this new phytase was compared with those of inorganic phosphorus or the commercially available microbial phytase (Natuphos™, BASF Corp., Mt. Olive, N.J.). Forty-eight weanling pigs were selected from multiparous sows at Cornell Swine Research Farm. The pigs were weaned at 21 days of age and fed a commercial creep feed until day 28. They were then placed two per pen with six pens assigned randomly per treatment. The pigs were given two weeks to adjust to the corn-soybean meal basal diet (Table 13).

TABLE 13

Formulation of the Experiment Diets for Pigs.

| Ingredient | +C % diet | −C % diet | YP % diet | MP % diet |
| --- | --- | --- | --- | --- |
| Corn | 60.5 | 61.57 | 61.07 | 61.07 |
| Whey Protein Concentrate | 3 | 3 | 3 | 3 |
| SBM 44% | 30 | 30 | 30 | 30 |
| Corn Oil | 3 | 3 | 3 | 3 |
| Lime | 0.8 | 0.93 | 0.93 | 0.93 |
| Di-calcium phosphate | 1.2 | 0 | 0 | 0 |
| Vitamin and Mineral premix | 0.5 | 0.5 | 0.5 | 0.5 |
| ECAP premix | 0 | 0 | 0.5 | 0 |
| MP premix | 0 | 0 | 0 | 0.5 |
| Salt | 0.5 | 0.5 | 0.5 | 0.5 |
| CSP 250 | 0.5 | 0.5 | 0.5 | 0.5 |
| Total | 100 | 100 | 100 | 100 |
| CP | 20.6 | 20.6 | 20.6 | 20.6 |
| Ca | 0.73 | 0.47 | 0.47 | 0.47 |
| $P_{total}$ | 0.6 | 0.39 | 0.39 | 0.39 |

Note:
All premixes use corn as the carrier
Vitamin and Mineral Premix supplies: 2,540 IU Vit. A, 660 IU Vit. D, 15 IU Vit. E, 2.2 mg Vit. K,
3.3 mg Riboflavin, 13.2 mg Pantothenic acid, 17.6 mg Niacin, 110.1 mg Choline, 1.98 ug B-12,
37.4 mg Mn, 0.6 mg I, 10 mg Cu, 0.3 mg Se, 100 mg Zn, and 100 mg Fe per Kg of diet Then, each pen received one of the four treatment diets. The positive control group (+C) received the basal diet supplemented with dicalcium phosphate. The negative control group (−C) received just the basal diet. The yeast phytase group (YP) received the basal diet supplemented with the expressed *E. coli* phytase at 1,200 U/kg of feed. The microbial phytase group (MP) received the basal diet supplemented with the BASF phytase at 1,200 U/kg of feed. Pigs were given free access to feed and water. Body weight gain of individual pigs was recorded weekly. Daily feed intake of individual pens was recorded daily. Blood samples from each of the individual pigs were taken weekly to assay plasma inorganic phosphorus concentrations. The results of body weight (BW), average daily gain (ADG), average feed intake (ADFI), and feed/gain ratio (F:G), and plasma inorganic phosphorus (PP) are presented in Table 14.

TABLE 14

Summary of PP, BW, ADG, ADFI, and F:G of Pigs as Effected by Dietary Phytase.[1]

| | +C | −C | YP | MP |
|---|---|---|---|---|
| | | Initial | | |
| PP | 12.99 | 13.02 | 13.07 | 13.54 |
| BW | 11.54 | 11.63 | 12 | 11.5 |
| | | Week 1 | | |
| PP | 10.83[A] | 6.48[C] | 8.59[B] | 8.35[B] |
| BW | 14 | 13.83 | 14.29 | 13.92 |
| ADG | .351 | .316 | .327 | .345 |
| ADFI | .700 | .684 | .697 | .697 |
| F:G | 2.04 | 2.20 | 2.18 | 2.13 |
| | | Week 2 | | |
| PP | 9.76[A] | 5.64[D] | 8.72[B] | 7.84[C] |
| BW | 18.04 | 17.42 | 17.83 | 17.71 |
| ADG | .578 | .512 | .506 | .542 |
| ADFI | .833 | .855 | .784 | .837 |
| F:G | 1.46[B] | 1.67[A] | 1.56[AB] | 1.55[AB] |
| | | Week 3 | | |
| PP | 11[A] | 6.26[C] | 8.64[B] | 8.13[B] |
| BW | 22.58 | 21.17 | 22 | 22.21 |
| ADG | .649[A] | .536[B] | .595[AB] | .643[AB] |
| ADFI | 1.166 | 1.02 | 1.001 | 1.003 |
| F:G | 1.8 | 1.92 | 1.71 | 1.36 |
| | | Week 4 | | |
| PP | 10.94[A] | 6.31[C] | 9.65[B] | 9.2[B] |
| BW | 27.54 | 25.29 | 27.79 | 27.38 |
| ADG | .708[AB] | .589[B] | .827[A] | .738[AB] |
| ADFI | 1.395[A] | 1.049[B] | 1.309[A] | 1.273[AB] |
| F:G | 1.98 | 1.87 | 1.59 | 1.73 |

[1]Numbers in the same row without sharing a common letter are significantly different. Analysis of difference was conducted with the Bonferroni (Dunn) T-tests with alpha = 0.05 and df = 20

In addition, there was severe phosphorus deficiency in the negative control group in the end of the four-week experiment. But, there was no sign of phosphorus deficiency in the other three groups. Clearly, the expressed *E. coli* phytase by *Pichia* was at least, if not more, effective as the commercial microbial phytase in improving bioavailability of phytate-phosphorus from the corn-soybean meal diets for weanling pigs. It can be used to replace inorganic phosphorus supplementation to weanling pigs.

Example 20

Effects of the Expressed *E. coli* AppA Phytase by *Pichia pastoris* on Iron (Fe) and Phytate Phosphorus Bioavailability to Weanling Pigs To determine the effect of the overexpressed *E. coli* phytase by *Pichia* on dietary phytate—bound Fe bioavailability to weanling pigs, 20 anemic pigs (21 days old and 7.3 g hemoglobin (Hb)/dL blood) were selected. The pigs were fed an Fe-deficient creep feed for 7 days and housed in metabolic cages at the age of 28 days old. The pigs were then fed the experimental diets at the age of 35 days old for 5 weeks. The treatment diets were as follows: Fe-deficient basal diet (−C, with added inorganic phosphorus), Fe-supplemented diet (+C), the Fe- and phosphorus-deficient diet supplemented with the expressed *E. coli* phytase (YP), or the commercial microbial phytase (BASF, MP) at 1,200 U/kg of feed. Body weight (BW), packed cell volume (PCV), Hb, and plasma inorganic phosphorus (PP) were determined weekly. The results are presented in Table 15.

TABLE 15

Summary of PCV, Hb, BW, and PP of Pigs as Effected by Dietary Phytase.[1]

| | +C | −C | YP | MP |
|---|---|---|---|---|
| | | Initial | | |
| PCV | 25 | 25 | 26 | 24 |
| Hb | 7.73 | 7.22 | 7.85 | 7.08 |
| BW | 8.14 | 8.27 | 8.17 | 7.45 |
| PP | 7.92 | 7.76 | 7.21 | 7.36 |
| | | Week 1 | | |
| PCV | 25 | 26 | 29 | 27 |
| Hb | 7.62 | 8.3 | 8.77 | 7.88 |
| BW | 9.44 | 8.84 | 9.63 | 8.57 |
| PP | 8.41 | 8.45 | 8.48 | 8.22 |
| | | Week 2 | | |
| PCV | 29 | 26 | 30 | 28 |
| Hb | 8.6 | 7.34 | 8.93 | 8.27 |
| BW | 12.32 | 10.13 | 11.91 | 10.84 |
| PP | 10.28[a] | 9.05[ab] | 8.89[ab] | 8.22[a] |
| | | Week 3 | | |
| PCV | 36[a] | 29[b] | 34[a] | 33[a] |
| Hb | 11.55[a] | 8.2[b] | 10.84[a] | 9.96[ab] |
| BW | 16.77[a] | 13[b] | 15.62[ab] | 14.62[ab] |
| PP | 12.14[a] | 11.37[ab] | 10.25[bc] | 9.71[c] |
| | | Week 4 | | |
| PCV | 39 | 34 | 38 | 36 |
| Hb | 12.99[a] | 10.11[b] | 12.27[a] | 11.35[ab] |
| BW | 21.36[a] | 17.37[b] | 19.44[ab] | 18.56[ab] |
| PP | 10.19[a] | 9.34[ab] | 9.49[ab] | 8.8[b] |
| | | Week 5 | | |
| PCV | 40 | 38 | 40 | 39 |
| Hb | 13.52[a] | 12.24[b] | 13.64[a] | 13.13[ab] |
| BW | 26.53 | 22.59 | 24.27 | 23.43 |
| PP | 9.27[a] | 8.95[ab] | 8.79[ab] | 8.02[a] |

[1]Values are means (n = 5). Means within the same row without sharing a common superscript ltter are significantly different (P < 0.10).

In conclusion, the overexpressed *E. coli* phytase by *Pichia* was at least as effective as the BASF phytase in improving phytate-phosphorus and Fe utilization in corn-soy diets for weanling pigs.

Although preferred embodiments have been depicted and described in detail herein, it will be apparent to those skilled in the relevant art that various modifications, additions, substitutions, and the like can be made without departing from the spirit of the invention and these therefore are considered within the scope of the invention as defined in the claims which follow.

What is claimed:

1. A method of producing phytase in yeast comprising:
providing a heterologous polynucleotide from a non-yeast organism which encodes a protein or polypeptide comprising a phytase from *Escherichia coli;*
expressing the polynucleotide in a yeast; and
isolating the expressed protein or polypeptide, wherein said protein or polypeptide catalyzes the release of phosphate from phytate and has increased thermostability as compared to that of said protein or polypeptide expressed in a non-yeast host cell.

2. The method according to claim 1, wherein the yeast is selected from the group consisting of *Saccharomyces* species, *Pichia* species, *Kluyveromyces* species, *Hansenula* species, *Candida* species, *Torulaspora* species, and *Schizosaccharomyces* species.

3. The method according to claim 2, wherein the yeast is *Pichia.*

4. The method according to claim 1, wherein the protein or polypeptide has an optimal phytase activity at a pH of less than about 4.

5. The method according to claim 1, wherein the protein or polypeptide preceded by a signal peptide is secreted by the yeast into a growth medium or is not secreted.

6. The method according to claim 5, wherein the protein or polypeptide is secreted by the yeast into the growth medium and has a concentration greater than 300 units per milliliter of the growth medium.

7. The method according to claim 1, wherein the heterologous polynucleotide which encodes the protein or polypeptide is spliced in frame with a transcriptional enhancer element.

8. The method according to claim 1, wherein the heterologous polynucleotide is carried on a vector for stable transformation.

9. The method according to claim 1, wherein the heterologous polynucleotide is carried on an artificial chromosome.

10. The method according to claim 1, wherein the heterologous polynucleotide is integrated into a chromosome of the yeast.

11. A yeast strain comprising:
a heterologous polynucleotide from a non-yeast organism which encodes a phytase from *Escherichia coli* and is functionally linked to a promoter, wherein the phytase catalyzes the release of phosphate from phytate and has increased thermostability as compared to a phytase expressed in a non-yeast host cell.

12. The yeast strain according to claim 11, wherein the yeast is selected from the group consisting of *Saccharomyces* species, *Pichia* species, *Kluyveromyces* species, *Hansenula* species, *Candida* species, *Torulaspora* species, and *Schizosaccharomyces* species.

13. The yeast strain according to claim 12, wherein the yeast is *Pichia.*

14. The yeast strain according to claim 11, wherein the heterologous polynucleotide which encodes the protein or polypeptide is spliced in frame with a transcriptional enhancer element.

15. The yeast strain according to claim 11, wherein the heterologous polynucleotide is carried on a vector for stable transformation.

16. The yeast strain according to claim 11, wherein the heterologous polynucleotide is carried on an artificial chromosome.

17. The yeast strain according to claim 11, wherein the heterologous polynucleotide is integrated into a chromosome of the yeast.

18. The yeast strain according to claim 11, wherein the protein or polypeptide is preceded by a signal peptide.

19. A vector comprising:
a polynucleotide from a non-yeast organism which encodes a protein or polypeptide comprising a phytase from *Escherichia coli;*
a promoter functionally linked to the polynucleotide encoding the protein or polynucleotide; and
an origin of replication to direct replication of the vector in yeast.

20. The vector according to claim 19 further comprising: a selectable marker.

21. The vector according to claim 20, wherein the selectable marker is selected from the group consisting of URA3, LEU2, TRP1, HIS3, HIS4, ARG4, and an antibiotic resistance gene.

22. The vector according to claim 19 further comprising:
an origin of replication to direct replication of the vector in a bacterial cell.

23. The vector according to claim 22, wherein the origin of replication is selected from the group consisting of ColE1, Ori, and oriT.

24. The vector according to claim 19, wherein the protein or polypeptide is preceded by a signal peptide.

25. The vector according to claim 19, wherein the polynucleotide which encodes the protein or polypeptide is spliced in frame with a transcriptional enhancer element.

26. Animal feed comprising the phytase made according to the method of claim 1.

27. The animal feed according to claim 26, wherein said phytase from *Escherichia coli* is an AppA phytase.

* * * * *

(12) INTER PARTES REVIEW CERTIFICATE (3025th)
United States Patent
Lei

(10) Number: US 7,312,063 K1
(45) Certificate Issued: Mar. 8, 2023

(54) OVEREXPRESSION OF PHYTASE GENES IN YEAST SYSTEMS

(75) Inventor: Xingen Lei

(73) Assignee: Cornell Research Foundation, Inc.

Trial Number:

IPR2019-00580 filed Jan. 23, 2019

Inter Partes Review Certificate for:

Patent No.: 7,312,063
Issued: Dec. 25, 2007
Appl. No.: 11/372,851
Filed: Mar. 10, 2006

The results of IPR2019-00580 are reflected in this inter partes review certificate under 35 U.S.C. 318(b).

INTER PARTES REVIEW CERTIFICATE
U.S. Patent 7,312,063 K1
Trial No. IPR2019-00580
Certificate Issued Mar. 8, 2023

AS A RESULT OF THE INTER PARTES REVIEW PROCEEDING, IT HAS BEEN DETERMINED THAT:

Claims 1-3 and 5-8 are cancelled.

\* \* \* \* \*

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 1
cggaattcgt cacctccgga ct                                        22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 2
cccaagcttc taagcaaaac actc                                      24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 3
cagctatgac catgattacg cc                                        22

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 4
cctagaacgg gaattcattg gccgcc                                    26

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
cccaagcttg atcacatcca ttca                                      24

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
cggggactgc tagcgcacgt tcgat                                     25

<210> SEQ ID NO 7
<211> LENGTH: 28

<212> TYPE: DNA
<213> ORGANISM: Artificial Sequence
<220> FEATURE:
<223> OTHER INFORMATION: Description of Artificial Sequence: Primer

<400> SEQUENCE: 7
atcgaacgtg cgctagcagc agtccccg                                28

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
gctctagact aagcaaaaca ctcc                                    24

<210> SEQ ID NO 9
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 9
ggggtaccat gggcgtctct gctgttctac ttcctttgta tctcctgtct ggagtcacct    60
ccggacagag tgagccggag                                         80

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
gggaattcat tacaaactgc aggc                                    24

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 11
ggaattccag agtgagccgg a                                       21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
ggggtacctt acaaactgca cg                                      22